(12) United States Patent
Van Hulle et al.

(10) Patent No.: US 10,364,518 B2
(45) Date of Patent: Jul. 30, 2019

(54) INTEGRALLY WOVEN OR KNITTED TEXTILE WITH POUCH AND METHODS OF MAKING THE SAME

(71) Applicant: ATEX Technologies, Inc., Pinebluff, NC (US)

(72) Inventors: Paul Van Hulle, Pinehurst, NC (US); Colleen Kaiser, Pinehurst, NC (US); Stephanie Booz Norris, Rocky Point, NC (US)

(73) Assignee: ATEX Technologies, Inc., Pinebluff, NC (US)

( * ) Notice: Subject to any disclaimer, the term of this patent is extended or adjusted under 35 U.S.C. 154(b) by 0 days.

(21) Appl. No.: 15/872,353

(22) Filed: Jan. 16, 2018

(65) Prior Publication Data

US 2018/0202082 A1   Jul. 19, 2018

Related U.S. Application Data

(60) Provisional application No. 62/445,908, filed on Jan. 13, 2017.

(51) Int. Cl.
*D04B 21/20* (2006.01)
*D03D 3/02* (2006.01)
(Continued)

(52) U.S. Cl.
CPC ............ *D04B 1/225* (2013.01); *A61F 2/06* (2013.01); *A61F 2/07* (2013.01); *D03D 3/02* (2013.01); *D03D 11/02* (2013.01); *D04B 21/20* (2013.01); *D04B 21/205* (2013.01); *A61F 2/04* (2013.01); *A61F 2002/072* (2013.01); *A61F 2002/075* (2013.01); *A61F 2210/0004* (2013.01); *A61F 2210/0076* (2013.01); *A61F 2240/001* (2013.01); *A61F 2250/003* (2013.01);
(Continued)

(58) Field of Classification Search
CPC ...... D10B 2509/06; D03D 3/02; D03D 11/02; D04B 21/205; A61F 2/04; A61F 2/06; A61F 2/07
See application file for complete search history.

(56) References Cited

U.S. PATENT DOCUMENTS

2003/0044155 A1   3/2003   Maiden
2007/0219622 A1   9/2007   Kuppurathanam
(Continued)

FOREIGN PATENT DOCUMENTS

CN   106109056 A    11/2016
GB      518181 A     2/1940
KR   20110096665 A    8/2011

OTHER PUBLICATIONS

PCT International Search Report for corresponding International Application No. PCT/US2018/013837, dated Jun. 11, 2018 (4 pages).
(Continued)

*Primary Examiner* — Dinah Baria
(74) *Attorney, Agent, or Firm* — Hoffmann & Baron, LLP

(57) ABSTRACT

An integrally woven or knitted textile, such as a tubular graft or sheet, having a base textile layer, in the case of a graft, it has at least one longitudinal tubular graft portion, and at least one pouch or flap integrally woven from at least a portion of the same set of yarns. Methods of making the same are also disclosed.

32 Claims, 23 Drawing Sheets

(51) Int. Cl.
  *A61F 2/07*   (2013.01)
  *D04B 1/22*   (2006.01)
  *A61F 2/06*   (2013.01)
  *D03D 11/02*  (2006.01)
  *A61F 2/04*   (2013.01)

(52) U.S. Cl.
  CPC ............... *A61F 2250/0096* (2013.01); *D10B 2403/0113* (2013.01); *D10B 2403/021* (2013.01); *D10B 2403/0222* (2013.01); *D10B 2501/061* (2013.01); *D10B 2509/06* (2013.01); *D10B 2509/08* (2013.01)

(56) References Cited

U.S. PATENT DOCUMENTS

2010/0106235 A1    4/2010  Kariniemi et al.
2017/0281331 A1*  10/2017  Perkins ................... A61F 2/07

OTHER PUBLICATIONS

PCT International Written Opinion for corresponding International Application No. PCT/US2018/013837, dated Jun. 20, 2018 (6 pages).

* cited by examiner

INTEGRALLY WOVEN OR KNITTED TEXTILE WITH POUCH AND METHODS OF MAKING THE SAME

CROSS-REFERENCE TO RELATED APPLICATIONS

This application claims the benefit of U.S. Provisional Application Ser. No. 62/45,908, filed Jan. 13, 2017, the contents of which are incorporated herein in their entirety.

FIELD OF THE DISCLOSURE

The present disclosure relates to medical textiles that include integrally woven or knitted pouches, optionally having a slit opening or openings to allow access to the space within the pouch, flaps and/or tabs. The pouch, flap and/or tab may be of any shape or dimension, and an element may be threaded into the pouch through the slit opening.

BACKGROUND

Medical devices for placement in a human or living body are well known in the art. Medical devices may include endoluminal devices such as stents, grafts, filters, coils, occlusion baskets, valves, and the like. A stent typically is an elongated device used to support an intraluminal wall. In the case of a stenosis, for example, a stent provides an unobstructed conduit through a body lumen in the area of the stenosis. Such a stent may also have a prosthetic graft layer of fabric or covering disposed about the inside and/or outside thereof. A stent having a graft layer is commonly referred to in the art as an intraluminal prosthesis, an endoluminal or endovascular graft (EVG), a stent-graft, or endograft.

Known grafts may be constructed by a weaving, knitting or other process, and optionally may incorporate two or more different types of materials, typically a non-metallic polymeric graft material and a radiopaque material, such as nitinol, which might be in the form of a wire. As depicted in FIG. 1, such a graft 20 may have incorporated the radiopaque wire 22 by either weaving it into the graft 20, or sewing it into the fabric using a suture 24. The graft can also be rolled over itself to form a cuff and sewn shut, to define a pocket between the inside and outside of the graft. These processes reduce productivity by increasing fabrication time by requiring the additional time for sewing of the wire into the graft or by having to thread the entire wire.

Thus, there is a need in the art for medical textiles having integrally woven or knitted pouches, flaps and/or tabs without the disadvantages of known grafts.

SUMMARY OF THE DISCLOSURE

A textile disclosed herein that has a first end, a second end and a length there between, containing at least one textile portion and at least one pouch portion. The textile may be woven or knitted from a set of yarns (staple fibers, continuous filaments, multifilaments, monofilaments, wire, or any material capable of being knit or woven) as flat, tubular, tapered, bifurcated, or any combination of the same. In an aspect of the inventive device, at least one pouch is woven or knitted from the same set of continuous filaments or a portion of the same set of warp ends as the textile and integrally woven or knitted with the textile. The pouch may be integrally joined to the textile at one side or multiple sides of the textile and at one side or multiple sides of the pouch.

The pouch may form any shape or dimension, such as straight, curved, crossed or helix sections or any combination of the same. Further, the pouch may be continuous and encompass the entire circumferential, horizontal or longitudinal textile segment or selective sections on the textile. One or more pouches may optionally contain a slit opening for access to the inside of the pouch. The slit opening may be positioned substantially parallel or perpendicular to the longitudinal, circumferential or diagonal axis of the graft portion. The slit openings may be located on an inner or an outer tubular wall of the pouch, and optionally, may be offset from each other, desirably by 180 degrees, but may also not be offset from each other, or offset by any useful degree, such as 45 degrees or 90 degrees.

In an embodiment, the pouch may contain open slit sections and closed sections. An element, such as a nitinol wire, may be threaded into the pouch using the slit opening or a pore of a closed section.

Typically, a woven graft includes a first set of yarns oriented in the end direction and a second set of yarns oriented in the pick direction, the sets being woven together to form the prosthetic textile. In the art of textile weaving, "end" yarns are oriented parallel to each other in an axial direction (also referred to as "warp ends" or "warp end yarns"), and are raised and lowered during the weaving process to provide a space for the "pick" yarns (also referred to as "weft yarns") to cross over and under as the pattern is woven. The pick yarns, being oriented perpendicularly to the end yarns in a lateral direction, are then carried in the pick direction in the provided space across the width of the ends by different types of mechanisms, for example by a shuttle, rapier, projectile, air jet or water jet, thereby weaving the prosthetic textile.

In constructing a graft from prosthetic textile, the yarns in the end and pick directions may be woven together in any weave configuration, for example plain, twill, satin, velour, double velour, basket weave or various customized configurations. The woven prosthetic material may be directly manufactured into a seamless tubular configuration having a trunk wall defining at least one lumen extending therethrough, and branched with two or more limbs extending from the graph body (e.g., it can be bifurcated or trifurcated). Such a seamless configuration may be manufactured using weaving methods known in the art, for example by employing a shuttle loom. The end yarns in the tubular configuration are oriented along the longitudinal axis of the tube or branch, while the pick yarns are oriented radially around the tube or branch.

Also disclosed is a method of making a medical textile containing at least one textile portion and at least one pouch portion sharing at least a portion of the same set of yarns (staple fibers, continuous filaments, multifilaments, monofilaments, wire, or any material capable of being woven or knitted). The textile can be woven or knitted as flat, tubular, tapered, bifurcated, or any combination of the same. This method may include the steps of: weaving or knitting a first textile portion; weaving or knitting a first pouch integrally with the first textile portion from at least a portion of said set of yarns; weaving or knitting a second textile portion integrally with the first textile portion and the first pouch from said set of yarns; weaving or knitting a second pouch integrally with the first textile portion, the first pouch and the second textile portion from at least a second portion of the set of yarns; and weaving or knitting a third textile portion integrally with the first textile portion, the first pouch, the second textile portion and the second pouch from said set of yarns, wherein each of the segments share at least a portion of the same set of yarns. For a woven textile, the yarns may include at least one set of warp end yarns and at least one set of weft yarns. In an embodiment, the textile portions and pouches may be woven from the same set of warp yarns. One or more shuttles or weft may be used in the method, preferably three shuttles or weft. In another embodiment, the textile portions and pouches may be knitted from more than one guide bars of yarn, preferably, a double needle bar. The pouch may have the same density or different density as the textile. The method may further comprise integrally forming, i.e., weaving or knitting, a slit opening in an outer or inner tubular wall of the pouch, and optionally threading an element, such as a radiopaque marker or nitinol stent, through the pouch via the slit opening. In an embodiment, the integrally woven or knitted textile may be made without cutting, sewing or stitching to form the pouch or the slit opening.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

BRIEF DESCRIPTION OF THE FIGURES

FIG. 3 includes yarn picks and yarn ends information for the weave.

FIGS. 7A and 7B depict an integrally woven graft having three longitudinal tubular graft portions, a circumferential pouch near the top, and a circumferential pouch near the bottom of the graft, both pouches having an opening therein. In FIG. 7B, a ring of nitinol wire may be threaded through the slit opening in each pouch and an exposed spine of nitinol wire may be visible down the side of the graft. Each circumferential pouch in FIGS. 7A-7D has one opening on a woven edge. FIG. 7C depicts an integrally woven graft having circumferential pouches throughout the graft length. As depicted in FIG. 7D, the tubular graft portions are woven according to weave pattern 101 of FIG. 2, and the circumferential pouches are woven according to weave pattern 102 of FIG. 3.

FIG. 8A contains two circumferential pouches around the complete exterior of the graft, while FIG. 8B contains shortened circumferential pouches that are not continuous around the graft. As depicted in FIGS. 8A and 8B, the tubular graft portions are woven according to weave pattern 101, as in FIG. 2, and the pouches are woven according to weave pattern 102, as in FIG. 3.

FIG. 10A is a weave pattern 104 for a modified 1×1 tubular graft. FIG. 10B is a two dimensional drawing of an integrally woven tubular graft containing two circumferential pouches, each having two slit openings woven therein, and diagonal pouches connected to the circumferential pouches along the graft length. FIG. 10C is a three dimensional diagram of an integrally woven tubular graft containing a circumferential pouch and a longitudinal spine pouch along the woven edge of the graft portion, wherein the spine and circumferential pouches contain a slit opening on the woven edge, and the pouches are not connected. FIG. 10D is a two dimensional diagram of an integrally woven tubular graft having two circumferential pouches and two longitudinal pouches, one longitudinal pouch along each woven edge of the graft. Each pouch has one slit opening woven therein and is not connected to other pouches. As depicted in FIGS. 10B and 10D, the tubular graft portions are woven according to weave pattern 101, as in FIG. 2, and weave pattern 104, as in FIG. 10A, and the circumferential and diagonal pouches are woven according to weave patterns 105 and 106, as in FIGS. 11A and 11B.

FIG. 11A is a weave pattern 105 for the left side of the longitudinal pouch, and FIG. 11B is a weave pattern 106 for the right side of the longitudinal pouch. FIG. 11C is a two dimensional drawing of an integrally woven tubular graft containing circumferential pouches with openings on the woven edge connected to longitudinal spine pouches. As depicted in FIG. 11C, the tubular graft portions are woven according to weave patterns 101 and 104, as in FIGS. 2 and 10A, respectively, the circumferential pouches are woven according to weave pattern 102, as in FIG. 3, and the longitudinal spine pouches are woven according to weave pattern 106.

FIG. 12A depicts a weave pattern 107 for the left side of the longitudinal spine pouch with a slit opening. FIG. 12B depicts a weave pattern 108 for the right side of the longitudinal spine pouch with a slit opening.

FIG. 12C is a two dimensional drawing of an integrally woven tubular graft containing two circumferential pouches with slit openings and two longitudinal spine pouches with slit openings, wherein the longitudinal pouches are woven on opposing sides of the graft relative to the woven edge, i.e., they do not wrap around the woven edge. FIG. 12D is a two dimensional drawing of an integrally woven tubular graft containing longitudinal spine pouches connected to a circumferential pouch on the top and bottom of a graft with each longitudinal spine pouch being woven on an opposing side of the graft relative to the woven edge. Each longitudinal pouch is connected to one circumferential pouch with a slit opening on a woven edge of an integrally woven longitudinal tubular graft portion. As depicted in FIGS. 12C and 12D, the tubular graft portions are woven according to weave pattern 101 and 104, as in FIGS. 2 and 10A, respectively, the circumferential pouches are woven according to weave pattern 102, as in FIG. 3, and longitudinal spine pouches woven according to weave pattern 107 and 108.

FIG. 14A represents a fully threaded and partially threaded knit notation pattern using traditional loop structures or lapping movements. FIG. 14B is a two dimensional drawing of the cross section of an integrally knitted textile containing pouches. FIG. 14C is a three dimensional depiction of the cross section at an angle for the knitted textile and pouch. FIGS. 14D and 14E are two dimensional drawings of front and top down views, respectively, of the knitted textile containing integrally knitted pouches.

FIG. 15A represents a partially threaded knit notation pattern. FIG. 15B is a two dimensional drawing of the cross section of a knitted textile containing integrally pouches. FIG. 15C is a three dimensional depiction of the angled cross section for the knitted textile and pouch. FIGS. 15D and 15E are two dimensional drawings of front and top down views, respectively, of the knitted textile containing integrally knitted pouches.

FIG. 16A represents a fully threaded knit notation pattern. FIG. 16B is a two dimensional drawing of the cross section of a knitted textile containing integrally pouches. FIG. 16C is a three dimensional depiction of the angled cross section for the knitted textile and pouch. FIGS. 16D and 16E are two dimensional drawings of front and top down views, respectively, of the knitted textile containing integrally knitted pouches.

FIGS. 17B and 17C are cross-sectional views of a circumferential pouch of FIG. 17A taken through the 17B-17B axis and 17C-17C axis, respectively. FIG. 17B shows one layer of woven or knitted material, whereas FIG. 17C shows two layers of woven or knitted material for the pouch with a slit opening and one layer of woven or knitted material for the flat textile around the pouch.

FIG. 18A is a flat textile containing a tab or flap connected to the flat textile on one side, and FIG. 18B is a flat textile containing a tab or flap connected to the textile on two sides.

DETAILED DESCRIPTION OF THE DISCLOSURE

Figure 1:
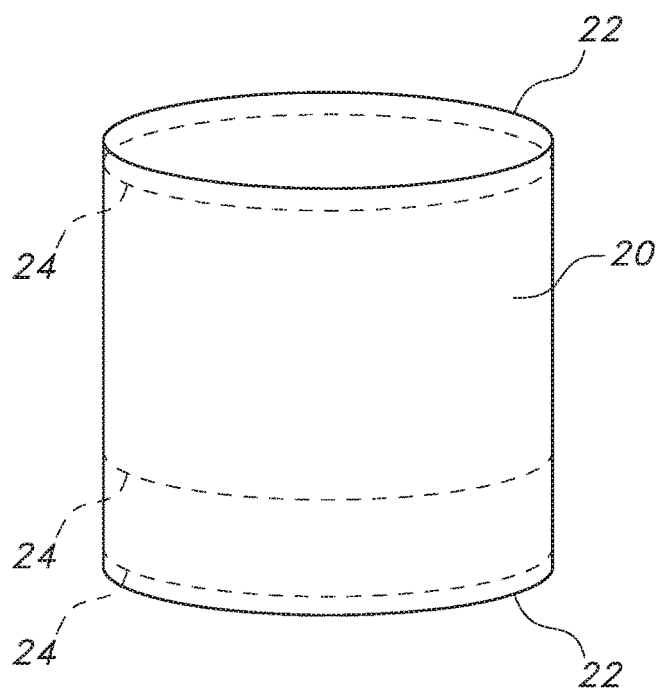
FIG. 1 depicts conventional tubular graft wherein a nitinol wire is held in place by stitching along the circumference at the top and the bottom of the tubular graft and along the wire spine.

The present disclosure solves problems known in the art by eliminating the need for cutting, sewing and creating seams on a medical textile, such as a graft or mesh to make a pouch, tab, flap, or extended textile segment integral within the medical textile. The pouch may incorporate an element, such as a radiopaque marker, device, drug, film, or any other compatible object. The present invention provides a method and device made therefrom which integrally weaves, knits, or a combination of weaves and knits, one or more exterior pouches, tabs, flaps, or extended textile segments on a medical textile, which may optionally be a tubular implantable graft. The pouch, tab, flap, or textile segment may be woven or knitted using one or more sets of yarns which also form the underlying textile, thereby integrally forming the pouch, tab or extended textile segment with the implantable textile. Each pouch may contain a slit opening, which also may be integrally woven or knitted into the textile, or it may be formed by other methods, such as by cutting. A slit opening may be utilized for elements to enter and exit the pouch, such as a radiopaque marker, device, drug, film, or any other compatible object.

When the textile is a tubular graft, the pouch may also be tubular and at least partially, substantially or completely circumscribes the underlying tubular graft. For example, the pouch may be donut-shaped about the underlying tubular graft. According to an embodiment, an element, such as a radiopaque marker (e.g., a wire), may be disposed or threaded through one slit opening in a pouch. By eliminating the step of having to sew the element into the graft, fabrication time and the associated cost are reduced. In addition, due to the seamless, integral formation of the pouch and graft, there is no puncturing of the polymeric graft material, and no seams. A "seam" is a line along which two pieces of material are joined together. In contrast, to make the graft of the present disclosure, the longitudinal tubular graft portion and pouch about the graft are joined by interweaving or interknitting whereby at least a portion of a set of yarns are shared between them; in other words, the segments are not made separately and then joined at a seam. Notwithstanding the advantage of seamless construction provided by the present invention, textile constructions which include seams may by integrated and used together with the present invention. For example, U.S. Pat. No. 6,994,724, which is incorporated by reference herein in its entirety, uses a textile construction which includes the dropping of ends to create various shapes and graft configurations and which also incorporate seams as part of its construction. Such a construction employing seams, as well as other constructions, may be used in combination with the present invention to manufacture a variety of products. A first embodiment relates to an integrally woven, knitted, or combination of woven and knitted textile having a first end, a second end, and a length there between. The textile may include: a base textile layer woven or knitted from a set of yarns, the yarns comprising a set of warp ends and/or a set of weft yarns; and an integrally woven or knitted pouch, tab or extended textile segment formed on the base textile layer, wherein the pouch, tab or extended textile segment is woven or knitted from at least a portion of the same set of yarns. The pouch, tab or extended textile segment may be woven or knitted from at least a portion of the same set of yarns or a subset of the yarns.

The textile may be any textile that may be used in an implantable medical device, such as a graft, tube, sheath, tether, patch, tape, mesh, valve, etc. The textile may be of any known shape or design and of any height and length, including bifurcated, trifurcated, tapered, panel, and sheet. For example, it may be a two-dimensional flat rectangle or tubular graft.

The terms "integrally woven" and "integrally knitted" mean the parts or segments of the textile are woven or knitted together to make the whole of the textile. In other words, the parts or segments of the textile share common yarns, either in total or in part.

A pouch may be an additional layer of fabric on the textile layer that has been woven or knitted and is integrally connected to the base textile layer. It may be woven or knitted so that it is closed on all sides where it connects to the base layer or connected on all but one or two sides. For example, for a rectangular pouch, it may be woven or knitted closed on two, three or four sides. Further, for a circular or oval pouch, it may be woven completely closed around the whole diameter or partially closed around the segments of the diameter. The same follows for any pouch shape, size or dimension.

A tab, flap or extended textile segment may be an additional layer of fabric that has been woven or knitted and is integrally connected to the base textile layer. It may be woven or knitted so that it is integrally attached to the base textile layer on at least one point. For example, for a rectangular tab, it may be woven or knitted closed on one or two of the four sides, or part of one or more sides. In the disclosure herein, a woven or knitted tab or extended textile segment or sac may be substituted for a woven or knitted pouch in any appropriate embodiment.

One or more tabs or pouches may be integrally woven or knitted into the base textile layer by means of modifying the plain weave or knit repeat pattern, according to any suitable weave or knit pattern. Each tab or pouch may be woven or knitted to be positioned linearly, curved, crossed, helically, or diagonally on the textile, or in any other suitable manner or shape. Each tab or pouch may extend across the entire length or height of the textile, or a part thereof. One or more tabs or pouches, which may be positioned linearly, curved, crossed, helically, diagonally or otherwise on the textile, are integrally woven or knitted with the base textile layer without a seam, sewing or cutting.

The textile may contain one circumferential pouch, tab, sac or extended textile segment. In another embodiment, the textile may comprise more than one pouch, such as two, three or four pouches woven or knitted therein. In some embodiments, combinations of pouch positions may be used, e.g., a linear pouch and a diagonal pouch on the same textile. In other embodiments, combinations of pouches, tabs and extended textile segments may be used on the same textile.

The positioning, width and length of the pouch, tab or extended textile segment are depended on application and intended use of the pouch, tab or extended textile segment. The precision of the pouch or tab size and placement is proportional to the weave or knit density and pattern repeat. The weave or knit density is tunable or adjustable to the pouch or tab application and use. In an embodiment, the density of tabs or pouches may be about 3 yarns per $cm^2$ to about 250 yarns per $cm^2$. As used herein, the density of yarns in a given area of textile refers to a number of yarns in one direction, e.g. weft yarns or picks for a weave and course yarns for a knit, plus a number of yarns a perpendicular direction, e.g., warp ends for a weave and wale yarns for a knit.

Each pouch, tab, flap or extended textile segment may be woven or knitted to be any width and any length. The maximum width for a pouch, tab or extended textile segment is proportionate to the weaving or knitting machine width. When more than one tab or pouch is included on the textile, the tabs or pouches need not be the same dimensions and may vary in size to accommodate a variety of uses and serve as housings for a variety of elements. In an embodiment, one or more tabs or pouches may be about 0.5 mm to about 200 mm wide, preferably 1 mm to about 10 mm wide, more preferably about 2 mm to about 8 mm, more preferably about 2 mm to about 6 mm, more preferably about 2 mm to about 4 mm, and still more preferably about 2.0 mm wide.

The width and length of each pouch, tab, flap or extended textile segment may be adjusted to accommodate the element threaded or otherwise placed therein. In an embodiment, it is desired for the element to fit securely and snuggly within the pouch with minimal friction and movement. In an embodiment, a coating may be applied to the element to reduce the friction and minimize the wear on the textile.

The base textile layer of the inventive device may be woven or knitted from a set of yarns and the pouch, tab or extended textile segment is woven or knitted from at least a portion of the same set of yarns. Yarn as used herein is a strand of textile fiber made up of one or more filaments. Thus, the yarns used in the exemplary embodiments may be constructed either from a single filament (monofilament), multiple filaments (multifilament), staple fibers, wire, or any other material capable of being woven or knitted. The filaments that comprise the yarn may be associated with each other in any manner, for example by being twisted around each other or interlaced. The yarns may be textured or flat, and may be of any opacity, for example bright, semi-dull, and full-dull. The yarns used to weave or knit the prosthetic textile device of the invention may be biologically compatible, for example natural materials such as silk and cotton, and synthetic materials such as polymers, for example polyethylene terephthalate (PET), ultra high molecular weight polyethylene (UHMWPE), polytetrafluoroethylene (PTFE), or other biocompatible polymer. Biologically incompatible yarn may also be used, such as cotton and the resulting prosthetic may be coated or otherwise treated with a suitable biocompatible material to permit enhance acceptance by and use in the body. The yarns may be resorbable, non-absorbable, or a combination thereof. The yarns may be made from a natural material, a synthetic material, a metal (e.g., gold, platinum, nickel, tin, nitinol, cobalt, chromium, stainless steel), or any combination thereof. In an embodiment, one or more of the yarns is polyester, nitinol or polypropylene. In another embodiment, the one or more yarns are polyester, preferably polyethylene terephthalate (PET).

The textile may be made up of yarns of one or more materials. The term yarns include both warp end yarns and weft (or pick) yarns. In an embodiment, the warp end yarns (or warp ends) and the weft yarns (or picks) are all the same material, for example PET. In another embodiment, the warp ends are one material and the weft yarns are comprised of more than one material. In an embodiment, the warp ends are PET, the weft yarns in the longitudinal tubular graft portions are PET, and the weft yarns in the pouch are PET and a metal, such as nitinol. In an embodiment thereof, the weft yarns used in the inner tubular wall of the pouch are PET, and the weft yarns used in the outer tubular wall of the pouch are nitinol. It is envisaged, that one might weave a different material via the weft yarns into the pouch for many different applications, for example for reinforcement purposes. Thus, stronger yarns, or biodegradable or absorbable material might be used in the weft yarns. Any number of alterations in changing the warp ends and weft yarns are envisaged in accordance with the disclosure.

In an embodiment thereof, the base textile layer and the one or more tabs or pouches may be woven or knitted from the same set of warp ends. In an embodiment, the pouch may be woven by using half of the warp ends in integrally weaving the inner tubular wall and the other half of the warp ends are integrally woven in the outer tubular wall. The warp ends are again used to weave any additional longitudinal tubular graft portions and so on for however many pouches are woven into the textile.

The yarns may have a linear density of about 40 denier (44 decitex) or higher, less than about 40 denier, about 30 denier, or less than about 30 denier total. Denier is the weight in grams of 9,000 meters of yarn. The thickness of the woven textile may be about 7 mil or less, about 6 mil to about 3 mil, about 4 mil or less, about 4.3 mil to about 5.5 mil, about 4.0 mil, or about 3.2 mil or less. A mil is a unit of length, in which 1 mil is equal to 0.001 inch. The thickness of the textile may be measured by standard tests (ISO 7198). The textile may have a number of threads per unit area of greater than or equal to about 10 yarns per $cm^2$, greater than or equal to about 100 yarns per $cm^2$, greater than or equal to about 150 yarns per $cm^2$, or greater than about 177 yarns per $cm^2$, greater than or equal to about 250 yarns per $cm^2$. The number of yarns is calculated by adding the number of warp yarns and the number of weft yarns in a unit area.

In one embodiment, the textile may be an ultra-thin, high density, low denier fabric comprising yarns of less than about 30 denier total and less than about 10 denier per filament; a number of threads per unit area of greater than about 177 yarns per $cm^2$; and a thickness of less than about 3.2 mil, such as that disclosed in U.S. Pat. No. 8,911,856, the contents of which are incorporated by references herein in its entirety. The fabric may weigh less than about 60 $g/m^2$. In another embodiment, the textile may be a low density flat sheet or tube comprising yarns of less than about 30 denier total and less than about 10 denier per filament; a number of threads per unit area of less than about 177 yarns per $cm^2$; and a thickness of less than about 3.2 mil. The low density textile may be woven or knitted where a pore of the textile may be used as an access point, for example, but not limited to, for introducing a pharmaceutical agent into a pouch, tab or flap. The weight of the fabric may be measured by standard test (ISO 7198).

Further, in one embodiment, the woven textile may have a water permeability rating of less than about 400 cc/min/$cm^2$ at 120 mm Hg pressure and/or a probe burst strength of about 20 lbs or greater. Probe burst strength can be determined by pressing a ⅜ inch probe into a one inch diameter portion of fabric at a speed of 0.5 inches per minute and measuring the force at which the probe bursts through the fabric (in accordance with ISO 7198, the contents of which is incorporated herein by reference). The woven textile may have a tensile strength of greater than about 25 lbs per inch.

Each pouch, tab or extended textile segment may have a slit opening woven or knitted therein. The slit opening may be manually cut, or formed integrally within the weave or knit of the tab or pouch rather than being cut after the fact.

Further, a pore or pores of a low density weave or knit may also be used as an access point to the pouch. Creating a slit in an outer tubular wall (or on the exterior side) of a tab or pouch provides access to the space between the underlying inner wall and the outer wall of the tab or pouch. When integrally woven or knitted, the slit opening is formed without having to cut the textile material to eliminate or minimize edges that might fray.

As such, a slit opening may be formed into one or more of the tabs or pouches. In one embodiment, the slit opening is formed by cutting. Such cutting may be performed by laser, blade, water jet or any other suitable method. In another embodiment, the slit opening is integrally woven into the tab or pouch. In an embodiment, the slit opening is positioned substantially parallel to a longitudinal axis of the textile; however, other positions of the slit, such as perpendicular to the longitudinal axis of the textile, or at another angle relative to the longitudinal axis of the textile, are contemplated.

The slit opening may be positioned in any location on the tab or pouch (for example, on an inner or an outer tubular wall). In another embodiment, the slit opening is in an outer wall of the pouch and extends across the pouch. In another embodiment, the slit opening may be subsequently closed by any method known in the art, e.g., by stitch, adhesive, or otherwise, in order to, for example, hold in position an element which has been placed in the pouch.

In an embodiment, an element is threaded through, or placed within, one or more slit openings. The element may be any object or device known for use in the art to have a therapeutic effect. It may also be a pharmaceutical drug product in any form suitable for placement in the pouch. The element may optionally be radiopaque, and may be any marker (e.g., a wire, disk, film), or stent known for use in the art. In other embodiments, the element is a sealing device, an inflatable device, an attachment ring with an anchoring device or barbs, a drug eluding structure, a biodegradable object, or a tube containing a liquid.

In an embodiment, the element is a radiopaque marker, which optionally may be a wire comprising a metal (e.g., gold, platinum, nickel, tin, nitinol, cobalt, chromium, or any combination thereof), though any material known for use in the art as a suitable radiopaque marker may be used with the present disclosure. In another embodiment, the radiopaque marker is a wire, preferably nitinol wire.

A second embodiment relates to an integrally woven graft having a first end, a second end and a length therebetween. The integrally woven graft comprises a longitudinal tubular graft portion woven from a set of yarns, and at least one tab or pouch woven from at least a portion of the same set of yarns and integrally woven with the longitudinal tubular graft portion. As such, the graft is made up of multiple segments. The graft may be of any known shape or design, including but not limited to, a straight longitudinal graft, a tapered graft, a flared graft, a stepped graft, a bifurcated or multifurcated graft, a fenestrated graft, or a combination of these shapes and configurations, e.g. a bifurcated graft having tapered and/or stepped portions. Similarly, the multiple segments of a graft may also vary in shape and construction within a single product. The graft may include one longitudinal tubular graft portion or, in other embodiments, multiple segments of longitudinal tubular graft portions that may be joined by one or more integrally woven pouches woven there between. Each longitudinal tubular graft portion has an inner wall and outer wall and a lumen therethrough. The longitudinal portions may be part of a graft design that also includes tapered, flared, stepped, flanged or multifurcated portions as part of the overall product.

The term "integrally woven graft" means that the parts or segments of the graft are woven together to make the whole of the graft. This is in contrast to grafts that are known in the art wherein a longitudinal tubular graft portion may be made separately from pocket or pouch portions, which are subsequently adhered or attached in some manner, e.g., sewn, to an end of the graft to house a wire or other element, or other known grafts that are folded over to make a pocket at an end thereof. The integrally woven graft is generally woven flat thereby when looking at it two dimensionally as a rectangle rather than in its expanded state with a hollow space in the middle, a woven edge that is both non-functional and non-permanent is created along the two sides of the tubular portion.

The integrally woven graft formed in accordance with the disclosure may be made to be any length and of any diameter. Optionally, the integrally woven graft may be made to be any length and of any diameter for implantation in any adult or infant animal. For example, the graft may be about 0.5 mm to about 600 mm in length. In an embodiment, the graft may be about 15 mm to about 250 mm in length, about 20 mm to about 140 mm in length, preferably about 20 mm to about 60 mm in length, and more preferably, about 20 mm to about 40 mm in length. The diameter as measured from the external graft wall surfaces may be about 0.1 mm to about 150 mm, about 5 mm to about 45 mm, preferably about 8 mm to about 40 mm, more preferably about 8 mm to about 30 mm, and still more preferably about 8 mm to about 20 mm.

Figure 2:
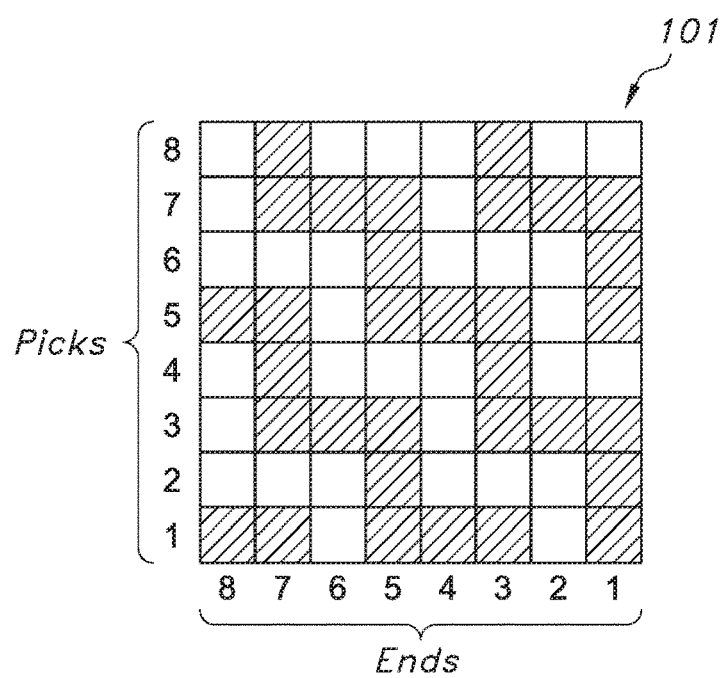
FIG. 2 is a two dimensional representation of a plain weave repeat pattern 101 used to create a three dimensional 1×1 tubular graft.

The longitudinal tubular graft portion of the graft includes a tubular body making up one or more segments of the woven graft. The longitudinal tubular graft portion may be woven by any means known in the art. In an embodiment, the longitudinal tubular graft portion is woven according to a plain weave repeat pattern (e.g., one over, one under, repeated), and preferably, a tubular weave repeat pattern 101, substantially, as shown in FIG. 2. Other weave patterns are useful.

FIG. 2 and other figures herewith depicting weave patterns use a symbolic notation to illustrate a particular weave pattern. Vertical columns of squares on the grid represent warp ends while horizontal rows of squares represent picks. A marked or filled-in square on the grid symbolizes that the warp end represented by that particular column is raised above the pick represented by that particular horizontal row. Leaving a square unmarked or blank means the warp end is lowered under the pick during weaving.

FIG. 2 represents the picks and ends for a flat woven tubular graft according to the invention. Picks 1, 2, 3 and 5 are used to weave the lower or bottom portion of the graft; and picks 4, 6, 7 and 8 are used to weave the upper or top portion of the graft.

In an embodiment, the pattern repeat is over the course of 8 warp ends versus a normal pattern of 4 warp ends. By changing the amount of ends woven in a repeat pattern, each inner and outer tubular wall are accounted for and woven. As per a regular tubular plain weave pattern, in order to create a plain tubular weave on the top and bottom of the graft, a total of 4 picks (2 on the top and 2 on the bottom) are needed. Since 4 layers are woven in the pouch in an embodiment of the present disclosure, 8 picks are used to practice the entire repeat: 4 picks on the top/bottom of the inner tubular wall and 4 picks on the top/bottom of the outer tubular wall.

In another embodiment, the longitudinal tubular graft portions may be woven from a set of weft yarns, and the one or more pouches are woven from at least a portion of the same set of weft yarns and at least one additional set of weft yarns. When the graft contains two pouches and multiple longitudinal tubular graft portions, the longitudinal tubular graft portions may be integrally woven from a first set of weft yarns, the first pouch may be integrally woven from at least a portion of the first set of weft yarns and a second set of weft yarns, and the second pouch may be integrally woven from at least a portion of the first set of weft yarns and either the second set of weft yarns or a third set of weft yarns.

Figure 3:
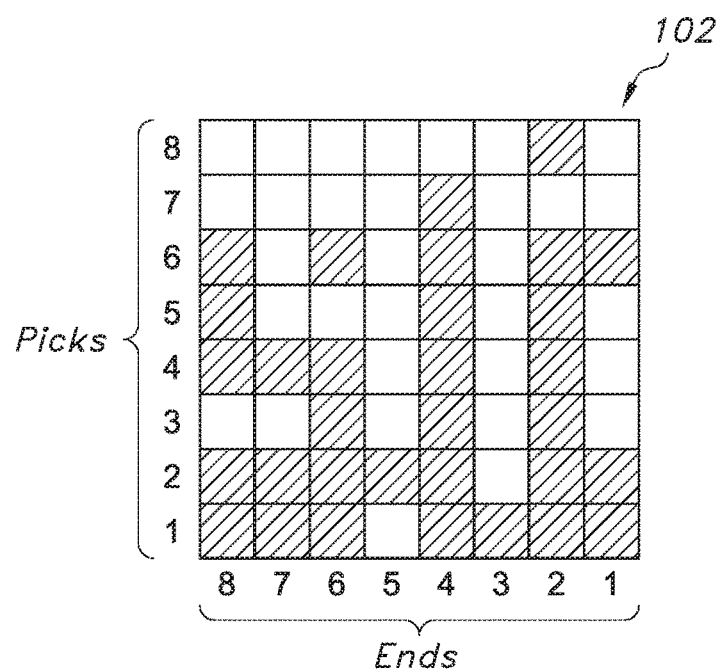
FIG. 3 is a two dimensional depiction of a weave pattern 102 developed for weaving a three dimensional circumferential pouch having at least one slit opening.

Any weft and warp end yarn may be used in accordance with the disclosure, for example with the weave patterns, substantially shown in FIGS. 2 and 3. It is also possible to alter the weft yarn used in one or more shuttles when weaving on a shuttle loom, or other weft insertion device when weaving is conducted on any other weaving machine known for use in the art, to create a colored pattern (if the yarns are different colors). In order to offer more shape stability to the graft, a stronger yarn or wire may also be used in the quill of a shuttle or other weft insertion device used in weaving the pouch.

One or more pouches may be woven into the longitudinal tubular graft portion by means of modifying the plain weave repeat pattern, according to any suitable weave pattern. The pouch or tab may be woven to follow the contours of the graft and may be positioned circumferentially, linearly, helically, or diagonally about the graft, or in any other suitable manner or shape. When the pouch is circumferentially positioned, the circumferential pouch (also referred to as a pocket or sac) extends around the entire circumference of the graft, or a part thereof. When the pouch extends around the entire circumference, it forms a circular tube. The one or more pouches, which may be positioned circumferentially, linearly, helically, diagonally or otherwise about the graft, are integrally woven with the longitudinal tubular graft portions, optionally on either side thereof, without a seam, sewing or cutting.

In an embodiment, the pouch is circumferentially or diagonally position about the graft and is woven according to a weave pattern 102, substantially as shown in FIG. 3. FIG. 3 depicts an 8×8 pattern (8 warp ends and 8 picks) that is repeated in the horizontal and vertical direction. The more repeats added in the horizontal direction, the wider the graft will be (i.e., the bigger the diameter), and the further around the circumference of the graft the pouch will extend. The more repeats added in the vertical direction, the further the pouch will extend along the longitudinal (length) direction of the graft. In the pattern, each column represents the weave pattern of an individual warp end and each row represents the weave pattern of an individual pick. The pattern is read from bottom to top (bottom row is the first pick woven). Picks 3-6 are the inner tubular wall. Picks 1, 2 and 7, 8 are the outer tubular wall. Two picks are used for weaving each tubular wall of the pouch. For the pouch, each column of ends can only be woven in a single layer, i.e., tubular wall. If the square is black or colored, the end is being raised. If the square is white, the end is being lowered. For example, in FIG. 3, looking at the pattern for End 1:

Picks 1 and 2 are used to weave the bottom outer tubular wall and the squares are black; therefore, the end is being raised and is not woven;

Pick 3 is used to weave the bottom inner tubular wall and the square is white; therefore the end is being lowered and is woven;

Pick 4 is used to weave the top inner tubular wall and the square is white; therefore the end is being lowered and is woven;

Pick 5 is used to weave the bottom inner tubular wall and the square is white; therefore, the end is being lowered and is woven;

Pick 6 are used to weave the top inner tubular wall and the square is black; therefore, the end is being raised and is woven;

Picks 7 and 8 are used to weave the top outer tubular wall and the squares are white; therefore the end is lowered and is not woven.

In an embodiment thereof, the longitudinal tubular graft portions and the one or more pouches are woven from the same set of warp ends. In this embodiment, more specifically, the pouch is woven by using half of the warp ends in integrally weaving the inner tubular wall and the other half of the warp ends are integrally woven in the outer tubular wall. The warp ends used in weaving the inner tubular wall should be kept separate from the warp ends being used in weaving the outer tubular wall to be sure that the pouch is woven to maintain a functional internal open area. All of the warp ends are then again used to weave any additional longitudinal tubular graft portions and so on for however many pouches are woven into the graft.

In an embodiment, the graft may contain one circumferential pouch. In another embodiment, the graft may comprise more than one pouch, such as two, three or four circumferential pouches woven therein. In some embodiments, combinations of pouch positions may be used, e.g., a circumferential pouch and a diagonal pouch on the same graft. Further, pouches may be positioned or located on the outer or inner wall of the textile or longitudinal tubular graft.

Figure 4:
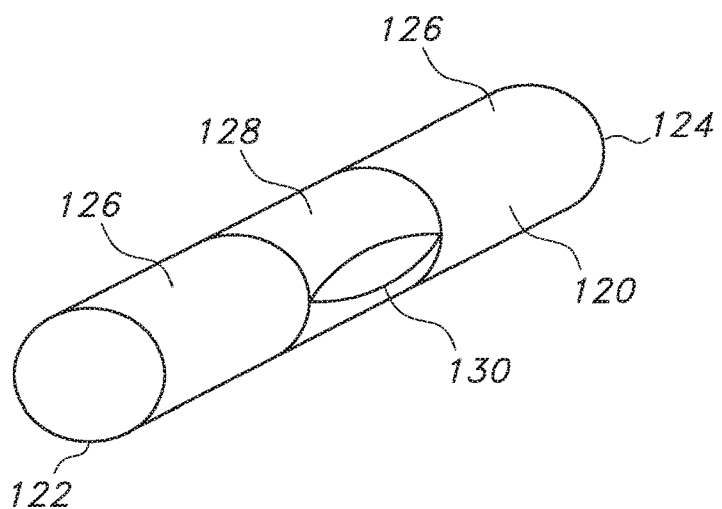
FIG. 4 depicts an integrally woven graft having a first end and a second end, made up of multiple segments, including longitudinal tubular graft portions and a circumferential pouch having a slit opening.

Shown in FIG. 4, the graft comprises: longitudinal tubular graft portions 126 with two ends 122 and 124, a circumferential pouch 128, and a slit opening 130 positioned substantially parallel to a longitudinal axis of the graft, interrelated as shown. The two ends 122 and 124 may be opposed open ends.

The slit opening 130 may be positioned in any location on the pouch (for example, on an inner or an outer tubular or textile wall). In FIG. 4, the slit opening is in an outer tubular wall of the pouch and extends across the pouch. Other positions of the slit opening 130, such as perpendicular to the longitudinal axis of the longitudinal tubular graft portion, or at another angle relative to the longitudinal axis of the longitudinal tubular graft portion, are contemplated.

Figure 5:
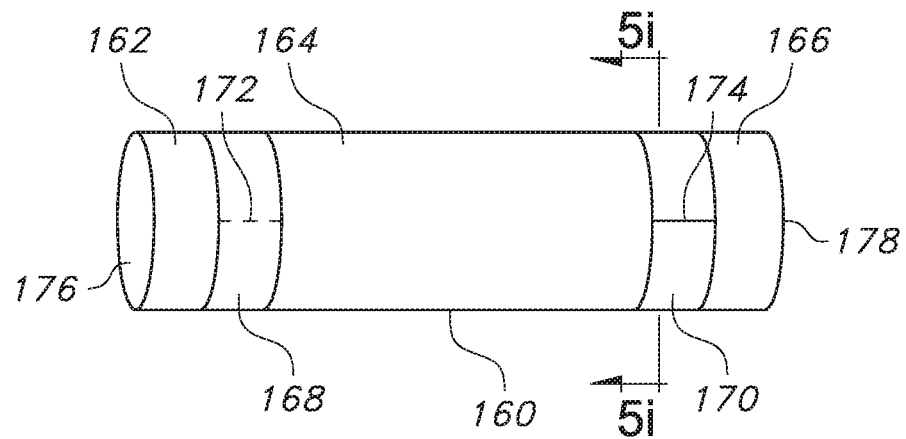
FIG. 5 is a two dimensional drawing of an integrally woven graft including longitudinal tubular graft portions and circumferential pouches with a slit opening at the back and a slit-opening at the front.
Figure 7A:
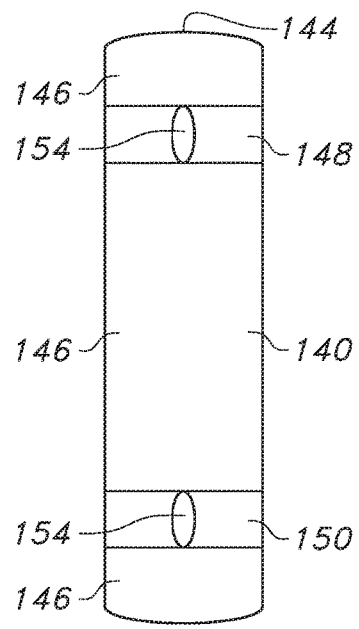
FIGS. 7A-7D are pictures and two dimensional drawings of an integrally woven tubular graft containing multiple circumferential pouches throughout the graft length.

In one embodiment, FIG. 5 is a side perspective view of an integrally woven graft 160, such as the one in FIG. 7A, including longitudinal tubular graft portions 162, 164, 166; circumferential pouches 168, 170, a slit opening 172 at the back or rear of the graft 160, and a slit-opening 174 at the front or side of the graft 160. When there are two pouches within the graft, the slit opening in a first pouch may be in-line with or offset from the slit opening in the second pouch. In an embodiment thereof, the slit opening in a first pouch may be offset by any useful degree, such as 45 degrees, 90 degrees or, desirably, 180 degrees, from the slit opening in the second pouch. When offset by 180 degrees, the slits will be on opposite sides of the graft. The graft 160 further includes opposed open ends 176, 178. More specifically, the longitudinal tubular graft portions 162, 164, 166 and circumferential pouches 168, 170 are woven from the same set of warp ends. The longitudinal tubular graft portions 162, 164, 166 are woven using the pattern 101, substantially as shown in FIG. 2, while circumferential pouches 168, 170 are woven using the pattern 102, substantially as shown in FIG. 3.

The longitudinal tubular graft portions 162, 164, 166 are woven from one set of weft yarns and each circumferential pouch 168, 170 is woven from a portion of the one set of weft yarns and at least one additional set of weft yarns. Longitudinal graft portions 162 and 166 are about 2 mm in longitudinal length, circumferential pouches 168, 170 are about 2.5 mm in longitudinal length and longitudinal tubular graft portion 164 is about 16 mm in longitudinal length. Woven slit opening 172 is about 2.5 mm in length at the back (e.g., 3:00 position) in circumferential pouch 168, and woven slit opening 174 is about 2.5 mm in length at the front (e.g., 9:00 position) in circumferential pouch 170.

Figure 6:
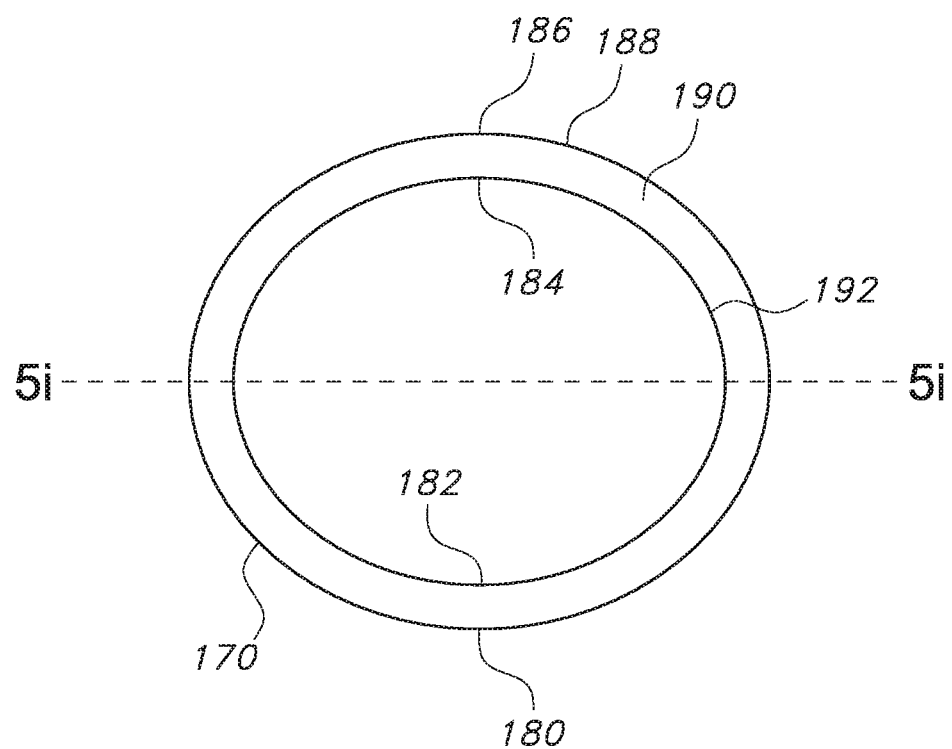
FIG. 6 is a cross-sectional view of a circumferential pouch of FIG. 5 taken through the 5*i*-5*i* axis shown therein and showing four layers of woven material. An outer tubular wall (also referred to as an exterior side), an inner tubular wall and an open inner tubular space are depicted.

In a further embodiment, the longitudinal tubular graft portion may be understood as a continuous inner tubular wall extending from the first end of the graft to the opposite end of the graft. In this case, a pouch is woven as an outer tubular wall around the inner tubular wall in the discrete areas. Each pouch has an inner tubular wall, an exterior side (or outer tubular wall) and an open inner tubular space. FIG. 6 shows cross-sectional view of a circumferential pouch 170 of FIG. 5 having an exterior side 188 (or outer tubular wall), an inner tubular wall 192 and an open inner tubular space 190. In an embodiment, shown in FIGS. 5 and 6, the longitudinal tubular graft portion 162, 164, 166 and the inner tubular wall 192 of the circumferential pouch 170 are continuous throughout the length of the graft 160, and the open inner tubular space 190 is external to the inner tubular wall 192.

FIG. 6 is a cross-section view of the graft 160 of FIG. 5 taken along the 5i-5i axis. The cross-sectional view of the graft 160 along the circumferential pouch 170 has four layers of woven material, as shown in FIG. 6; while a cross-sectional view of the longitudinal tubular graft portion has two layers of woven material, i.e., an outer wall and an inner wall (not shown). Those four layers are shown in the embodiment of FIG. 6 as bottom outer tubular wall 180, bottom inner tubular wall 182, top inner tubular wall 184, and top outer tubular wall 186.

In an embodiment, to weave the pouch of FIG. 6, the bottom outer tubular wall 180 or the top outer tubular wall 186 must be woven first. If the bottom outer tubular wall 180 is woven first, then the bottom inner tubular wall 182 is woven before weaving the top inner tubular wall 184. Once the top inner tubular wall 184 is woven, the top outer tubular wall 186 of the pouch 170 can be woven. The exact opposite of this is also true, as long as the correct order is followed.

Figure 7B:
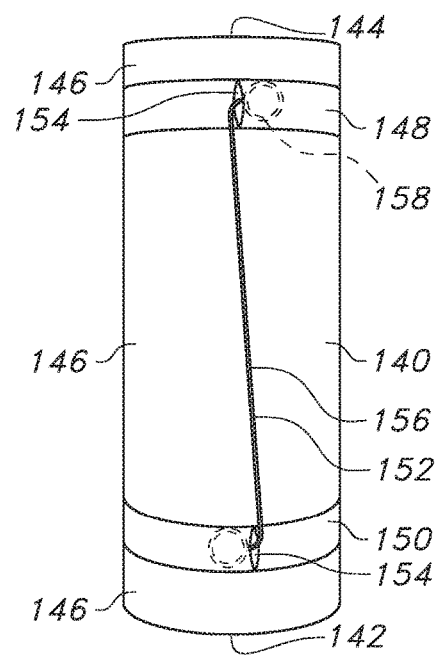

When the graft comprises two or more pouches, none or any number of the pouches may be circumferentially positioned about the graft, each may be referred to as "a circumferential pouch." In an embodiment, shown in FIGS. 7A and 7B, the graft 144 comprises two circumferential pouches 148 and 150, with one being near (i.e., proximal to) a first end of the graft and a second pouch being near (i.e., proximal to) the opposite end of the graft or away from (i.e., distal to) a first end of the graft. Near the end means that the circumferential pouch is positioned closer to the end of the graft than to the mid-point of the graft. In an embodiment, when the graft is about 25 mm in length, each pouch may be positioned about 2 mm to about 4 mm, preferably about 2 mm, from each end of the graft and each pouch is about 2 mm to about 4 mm, preferably about 2 mm to about 3 mm, and more preferably about 2.5 mm, wide. The circumferential pouch may be woven to be any width. When more than one pouch is included on the graft, the pouches need not be the same dimensions and may vary in size and position to accommodate a variety of uses and serve as housings for a variety of elements.

In an embodiment, when the graft comprises one or more pouches, one or more wires (radiopaque or not) may be disposed, for example threaded, through a slit opening or more than one slit opening in each pouch or two wires (radiopaque or not) may be used, with one wire being threaded through the slit opening in the first pouch and a second wire being threaded through the slit opening in the second pouch. In a certain embodiment, FIGS. 7A and 7B depict an integrally woven graft 140 having three longitudinal tubular graft portions 146, a circumferential pouch 148 near the top, and a circumferential pouch 150 near the bottom of the graft, both pouches 148, 150 having an opening 154 therein. In FIG. 5B, a ring 158 of nitinol wire 152 may be threaded through the slit opening 154 in each pouch 148, 150 and an exposed spine 156 of nitinol wire 152 is visible down the side of the graft 140.

One such nitinol wire 152 may be threaded through each slit opening 154 in each circumferential pouch 148, 150 woven in the graft 140. The present invention, however, is not limited to the shape of the nitinol wire depicted in FIG. 7B, and any suitable shape may be used. Further, wire 152 is not limited to nitinol wire, and any suitable wire materials may be used.

Figure 7C:
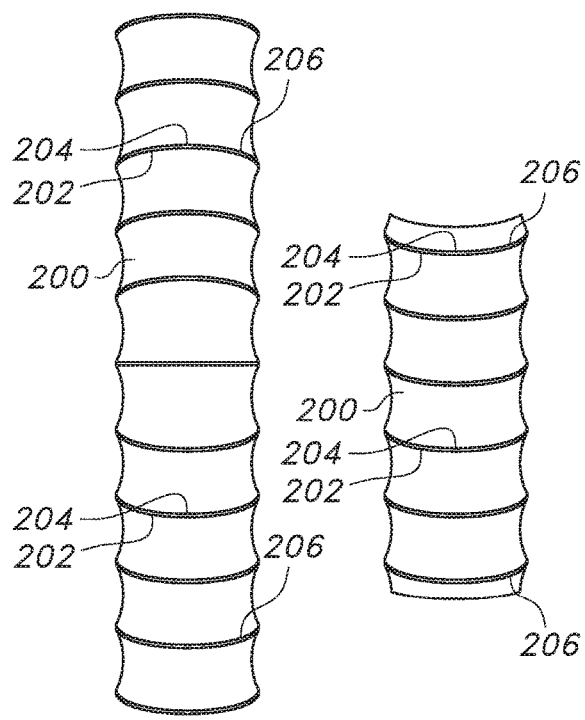
Figure 7D:
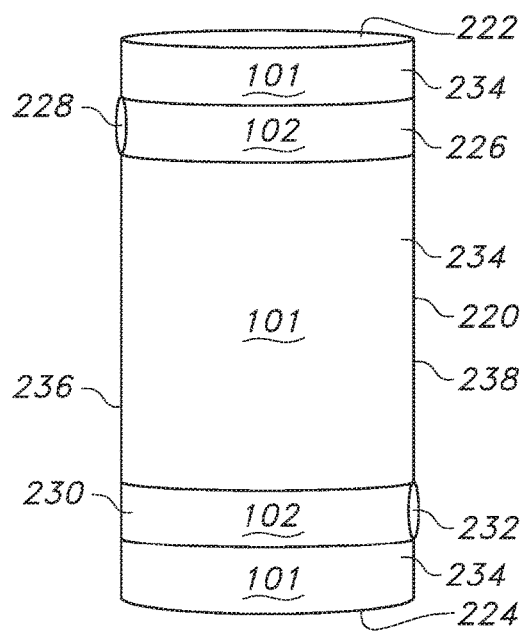

FIGS. 7C-7D are two dimensional drawings of integrally woven tubular grafts containing multiple circumferential pouches throughout the graft length. These pouches may be evenly positioned circumferentially through the length of the graft or woven to be positioned at any length of the graft. Each circumferential pouch, in FIGS. 7A-7D, has one opening on a woven edge. As depicted in FIG. 7C, integrally woven graft 200 contains multiple circumferential pouches 202. Each pouch 202 is depicted as having a circumferential wire 204 disposed there within via a pouch opening 206. As depicted in FIG. 7D, woven graft 220 includes opposed open ends 222, 224; circumferential pouches 226, 230; and longitudinal tubular graft portions 243. Circumferential pouch 226 of the woven graft 220 of FIG. 7D has one opening 228 on a woven edge 236; and the circumferential pouch 230 of the woven graft 220 of FIG. 5 has one opening 232 on a woven edge 238. As depicted in FIG. 7D, the tubular graft portions are woven according to weave pattern 101, as in FIG. 2, and the circumferential pouches are woven according to weave pattern 102, as in FIG. 3.

Figure 8A:
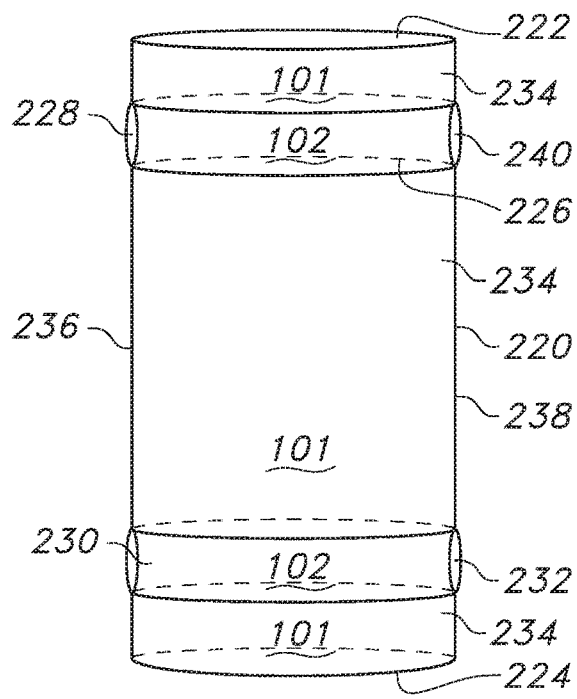
FIGS. 8A and 8B are two dimensional drawings of an integrally woven tubular graft with circumferential pouches that have two slit openings, with one slit opening on each woven edge.
Figure 8B:
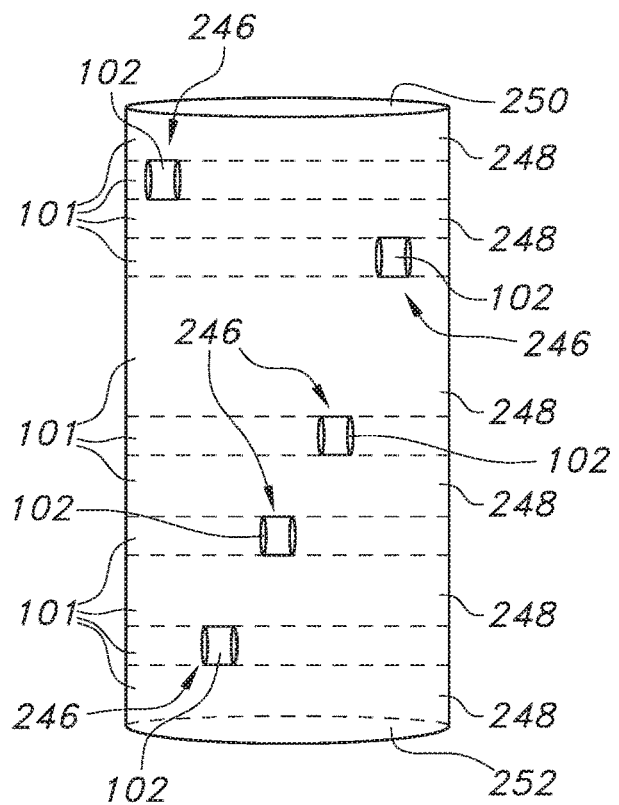

In another embodiment, as depicted FIGS. 8A and 8B, the circumferential pouch 226 and 246 have two slit openings 228, 240. Pouch slit opening 228 is on each woven edge 236, and pouch opening 240 is on woven edge 238. FIG. 8B is a two dimensional drawing of an integrally woven tubular graft 244 containing shortened circumferential pouches 246 that are not continuous around the graft 244. Woven graft 244 includes opposed open ends 250, 254; and longitudinal tubular graft portions 248. Application of each pouch or sac determines the location and size of each pouch. As depicted in FIGS. 8A and 8B, the tubular graft portions 234 and 244 are woven according to weave pattern 101 as in FIG. 2, and the pouches 226 and 246 are woven according to weave pattern 102 as in FIG. 3.

Figure 9A:
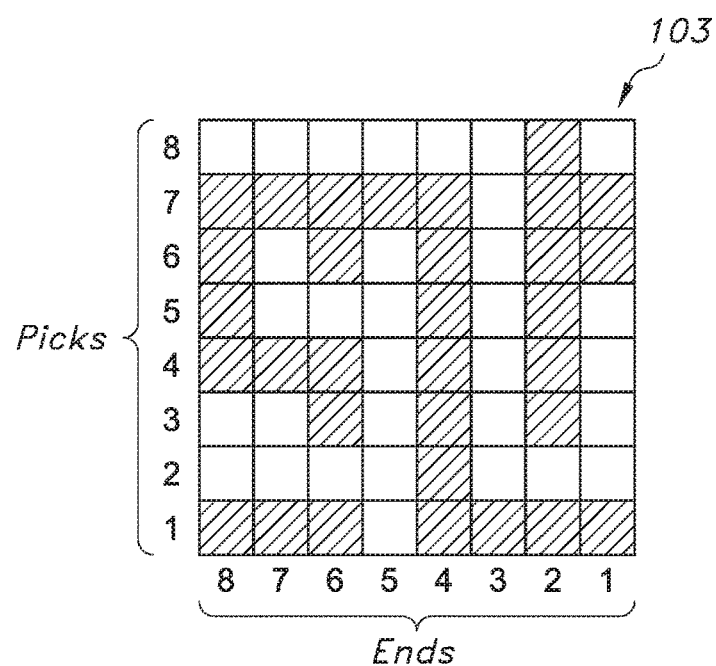
FIG. 9A depicts a weave pattern 103 for a continuous circumferential pouch with no slit openings.
Figure 9B:
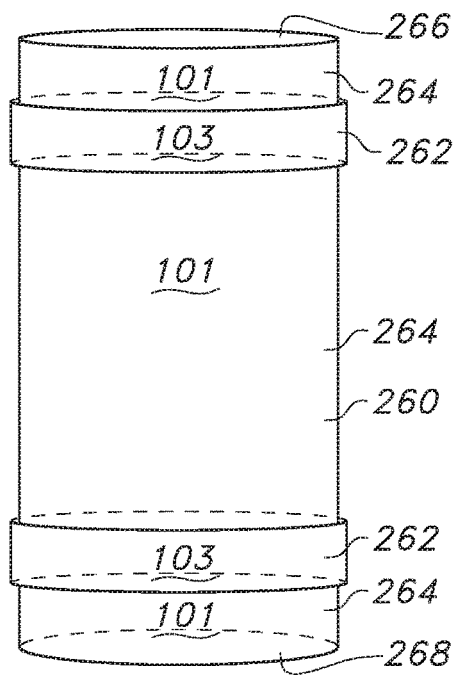
FIG. 9B depicts a two dimensional drawing of an integrally woven tubular graft containing continuous circumferential pouches with no slit openings woven therein. As depicted in FIG. 9B, the tubular graft portions are woven according to weave pattern 101, as in FIG. 2, and the circumferential pouches are woven according to weave pattern 103, as in FIG. 9A.

FIGS. 9A-9B and 10A-10D are weave patterns and drawings of an integrally woven tubular graft containing multiple circumferential, longitudinal and diagonal pouches throughout the graft length. FIG. 9A is a weave pattern 103 for a continuous circumferential pouch with no slit opening. FIG. 9B is a two dimensional drawing of an integrally woven tubular graft 260 containing circumferential pouches 262 with no slit openings woven therein. Woven graft 260 includes opposite open ends 266, 268; and longitudinal tubular graft portions 264. As depicted in FIG. 9B, the tubular graft portions 264 are woven according to weave pattern 101 as in FIG. 2, and the circumferential pouches 262 are woven according to weave pattern 103 as in FIG. 9A.

Figure 10A:
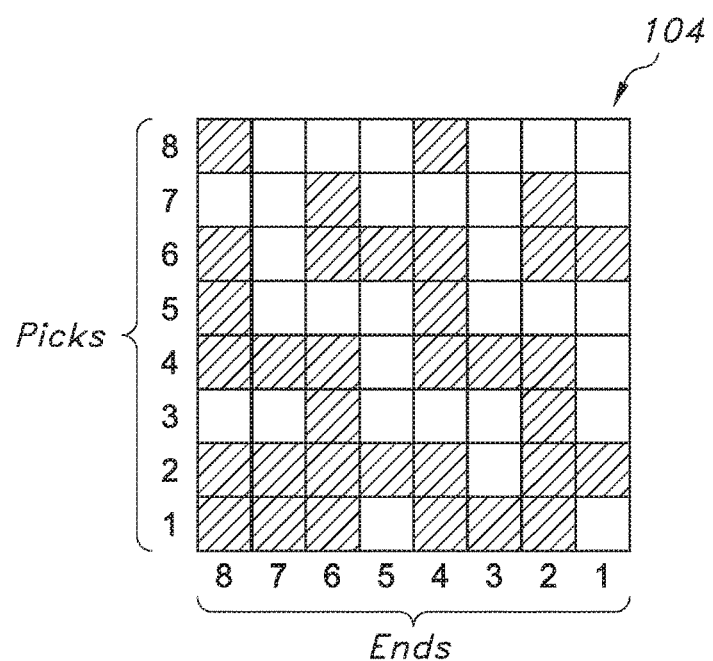
FIGS. 10A-10D are weave patterns and drawings of an integrally woven tubular graft containing multiple circumferential, longitudinal and diagonal pouches throughout the graft length.
Figure 10B:
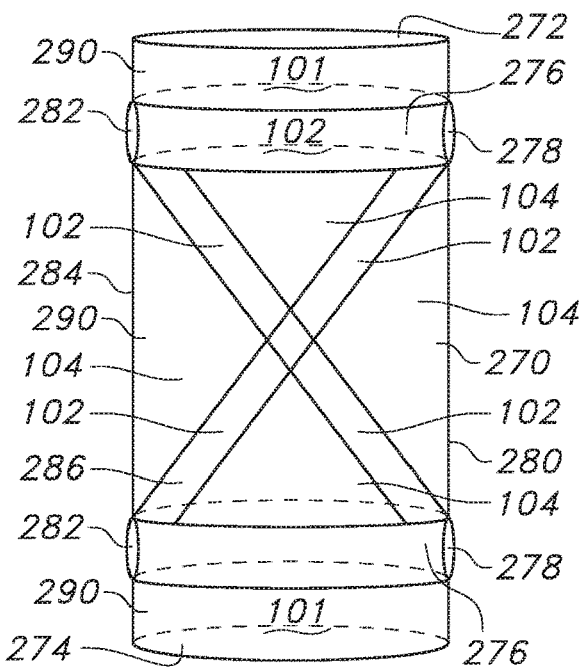

FIG. 10A is a weave pattern 104 for a modified 1×1 tubular graft. A regular 1×1 plain weave pattern tacks the graft closed, and the modified weave pattern does not tack the graft shut. FIG. 10B is a two dimensional drawing of an integrally woven tubular graft 270 having opposed open ends 272, 274. Graft 270 contains two circumferential pouches 276 each depicted as having two openings 278, 282 woven therein. Pouch opening 278 may be disposed at woven graft edge 280, and pouch opening 282 may be disposed at woven graft edge 284. Pouch openings 278, 282; however; may be suitably disposed at other locations for the woven graft 270. Moreover, the number of pouch openings may vary from greater than two, less than two—including no opening. Woven graft 270 may include one or more diagonal pouches 286 along at least a portion of the longitudinal length of the graft 270. The diagonal pouches 286 may be woven such that their open ends coincide with portions of the circumferential pouches 276, as depicted in FIG. 10B. The diagonal pouches 286, however, may be disposed along any portion of the graft 270. The angle of the diagonal pouch 286 with respect a longitudinal extent of the graft 270 may be constant or may vary. Suitable angles may vary from about 10 degrees to about 80 degrees, including from about 30 degrees to about 60 degrees or even about 45 degrees. Moreover, while the circumferential pouches 276 are depicted as being substantially perpendicular to a longitudinal extend of the graft 270, other orientations may suitably be used. For example, circumferential pouches 276, as well as any of the other circumferential pouches described herein, may be slightly off perpendicular, for example about 10 degrees or less than 10 degrees acute from a longitudinal extend of the graft 270. As depicted in FIG. 10B, the tubular graft portions 288 may be woven according to weave pattern 101, as in FIG. 2, and the tubular graft portion 290 may be woven to the weave pattern 104 as in FIG. 10A. The circumferential pouches 276 and the diagonal pouches 286 may be woven according to weave pattern 102, as in FIG. 3.

Figure 10C:
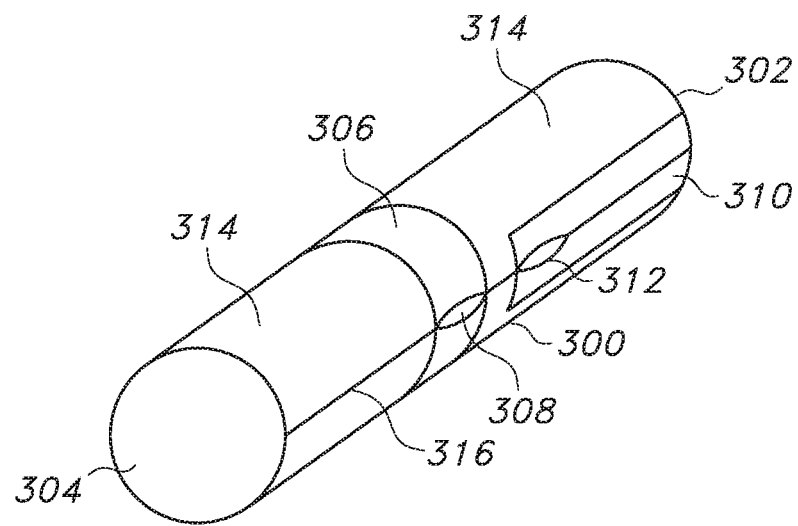

FIG. 10C is a perspective view of an integrally woven tubular graft 300 containing a circumferential pouch 306 and a longitudinal spine pouch 310. The tubular graft 300 has opposed open ends 302, 304. The circumferential pouch 306 may have an opening 308, and the longitudinal spine pouch 310 may have an opening 312. Either or both openings 308, 312 may be disposed along a woven edge 316 of the graft 300. Desirably, the spine pouch 310 and circumferential pouch 306 each contain their slit openings 312, 308 on the woven edge 316 and are not connected. The graft 300 also includes non-pouch portions 314 of the graft 300.

Figure 10D:
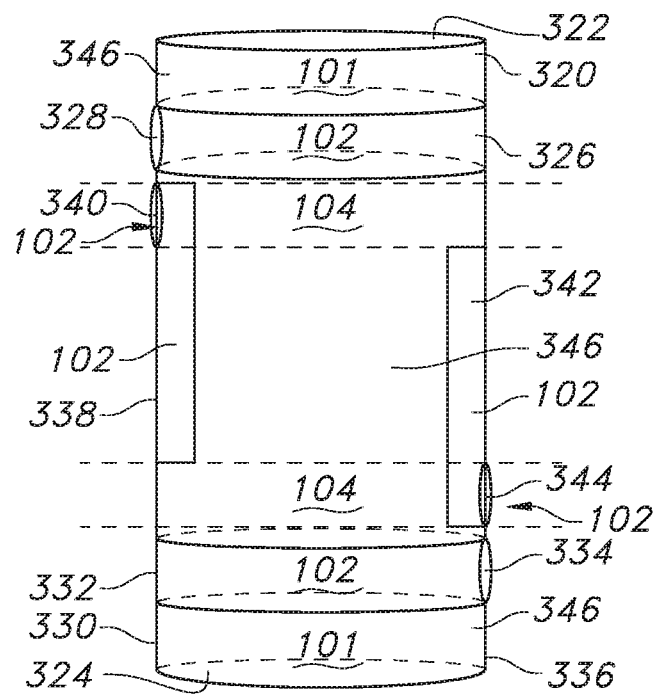

FIG. 10D is a two dimensional diagram of an integrally woven tubular graft 320 having opposed open ends 322, 324; two circumferential pouches 326, 332; and two longitudinal pouches 338,342. As depicted in FIG. 10D, circumferential pouch 326 has a pouch slit opening 328 along a woven edge 330 of the graft 320; circumferential pouch 332 has a pouch slit opening 334 along a woven edge 336 of the graft 320; longitudinal pouch 338 has a pouch slit opening 340 along the woven edge 330; and longitudinal pouch 342 has a pouch slit opening 344 along the woven edge 336. Each pouch 326, 332, 338, 342 has one opening woven 328, 332, 340, 344 therein, respectively, and is not connected to any other pouch. Tubular non-pouch graft portions 346 may be woven according to the weave patterns 101 and 104 as in FIGS. 2 and 10A. The circumferential pouches 326, 332 and the longitudinal pouches 338, 342 may be woven according to weave pattern 102 as in FIG. 3.

Figure 11A:
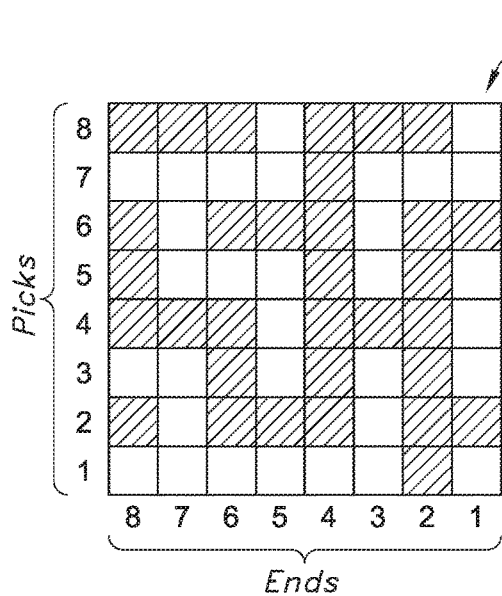
FIGS. 11A-11C are weave patterns and drawings of integrally woven tubular graft containing longitudinal spine pouches.
Figure 11B:
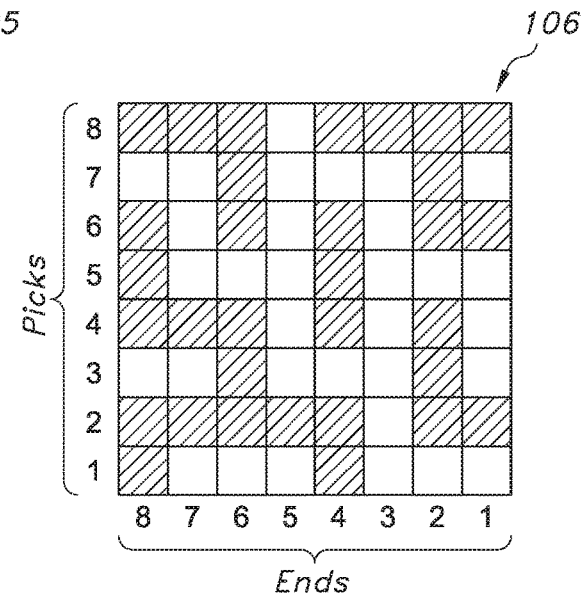
Figure 11C:
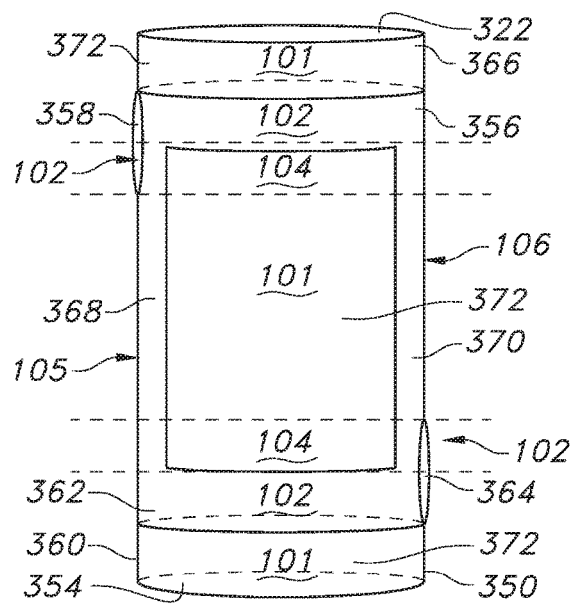

FIGS. 11A-11C and 12A-12D are weave patterns and drawings of longitudinal spine pouches. FIG. 11A depicts a weave pattern 105 for the left side of the longitudinal pouch 368. FIG. 11B depicts a weave pattern 106 for the right side of the longitudinal pouch 370. FIG. 11C is a two dimensional drawing of an integrally woven tubular graft 350 having opposed open ends 352, 354 and containing circumferential pouches 356, 362 with openings 358, 364 on the woven edges 360, 366, respectively, and connected to longitudinal spine pouches 368, 370. As depicted in FIG. 11C, the non-pouch tubular graft portions 372 are woven according to weave patterns 101 and 104 as in FIGS. 2 and 10A, respectively, and the circumferential pouches 356, 362 are woven according to weave pattern 102 as in FIG. 3.

Figures 12A, 12B:
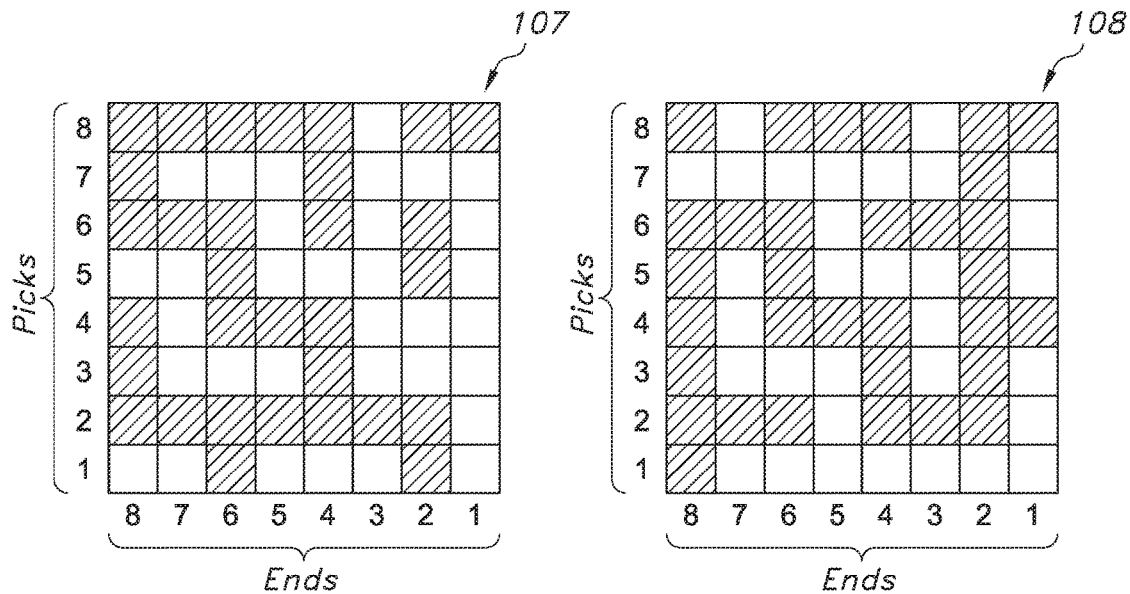
FIGS. 12A-12D are weave patterns and drawings of integrally woven tubular graft containing longitudinal spine pouches with slit openings.
Figure 12C:
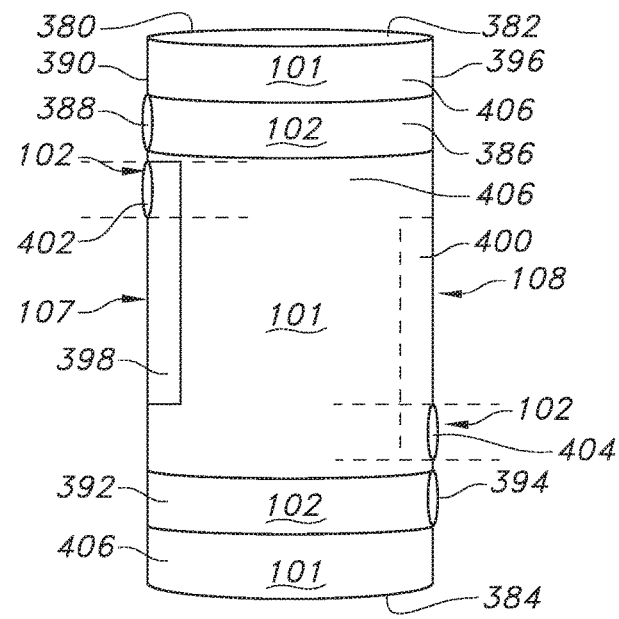

FIGS. 12A-12D are weave patterns and drawings of integrally woven tubular graft containing longitudinal spine pouches with slit openings. FIG. 12A depicts a weave pattern 107 for the left side of the longitudinal pouch 398 with the slit opening 402. FIG. 12B depicts a weave pattern 108 for the right side of the longitudinal pouch 400 with the opening 404. FIG. 12C is a two dimensional drawing of an integrally woven tubular graft 380 having opposed open ends 382, 384 and containing two circumferential pouches 386, 392 with openings 388, 394, respectively. The graft 380 further contains two longitudinal spine pouches 398, 400 with openings 402, 404, respectively. The longitudinal pouches 398, 400 are woven on opposing sides or edges 390, 396 of the graft relative to the woven edge, i.e., they do not wrap around the woven edge.

Figure 12D:
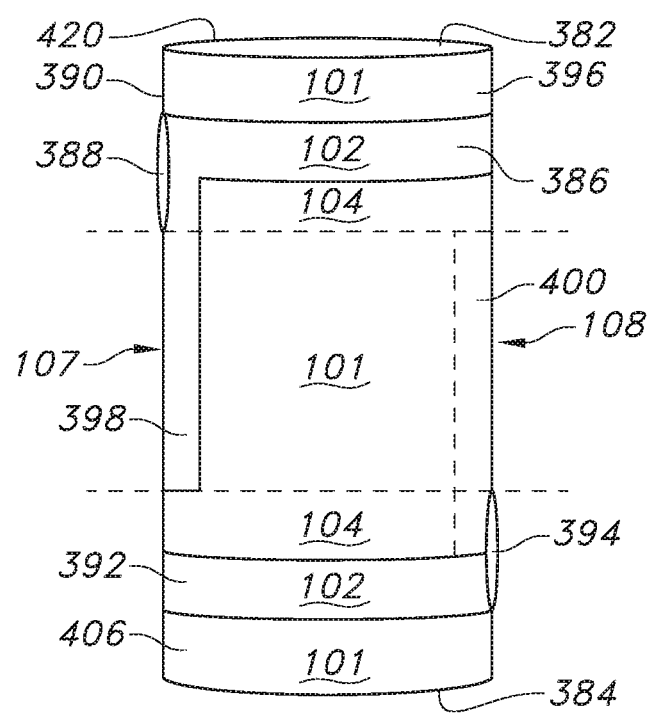

FIG. 12D is a two dimensional drawing of an integrally woven tubular graft 420 containing a longitudinal spine pouch 398 connected to a circumferential pouch 386 located proximal to the top of the graft 420 in FIG. 12D and a longitudinal spine pouch 400 connected to a circumferential pouch 392 located proximal to the bottom of a graft 420 in FIG. 12D. Each longitudinal spine pouch 398, 400 is woven on opposing sides or edges 390, 396 of the graft 420 relative to the woven edges 390, 396. Each longitudinal pouch 398, 400 is connected to one circumferential pouch 386, 392, respectively, with an opening 388, 394, respectively, on a woven edge 390, 396 of the integrally woven longitudinal tubular graft 420. As depicted in FIGS. 12C and 12D, the tubular graft portions are woven according to weave pattern 101 and 104, as in FIGS. 2 and 10A, respectively, the circumferential pouches are woven according to weave pattern 102, as in FIG. 3, and longitudinal spine pouches woven according to weave pattern 107 and 108.

Figures 13A, 13B:
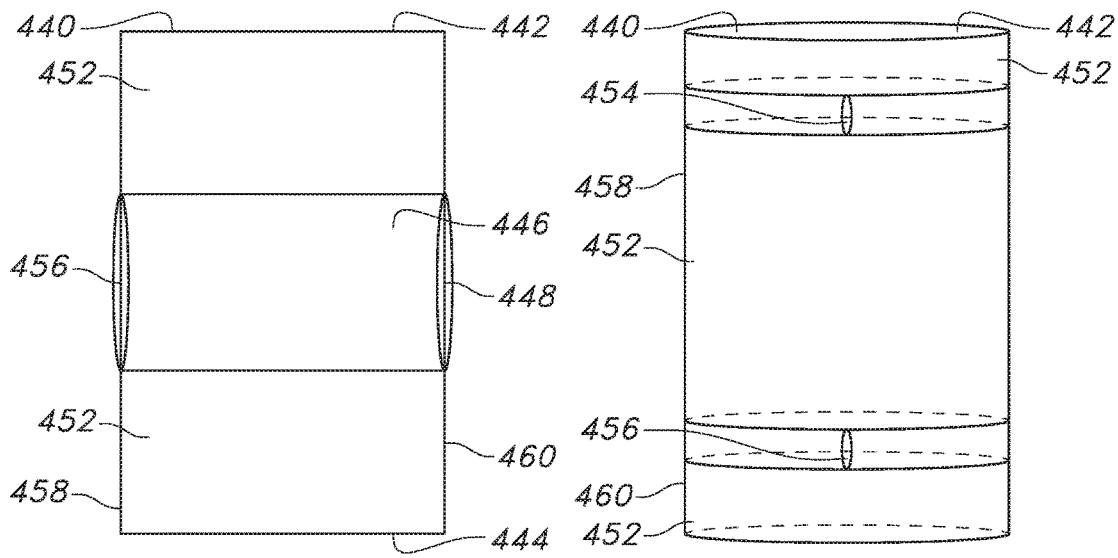
FIGS. 13A-13D are non-limiting exemplary drawings of integrally woven textiles containing one or more pouches of the present disclosure.

FIGS. 13A through 13D are non-limiting exemplary drawings of integrally woven textiles containing one or more pouches of the present disclosure. In FIG. 13A, integrally woven graft 440 has opposed open ends 442, 444 and an elongated or enlarged circumferential pouch 446 disposed with non-pouch graft portions 452. The circumferential pouch 446 may have two integrally woven pouch slit openings 448, 450 at the corresponding woven edges 460, 458 of the graft 440.

Figures 13C, 13D:
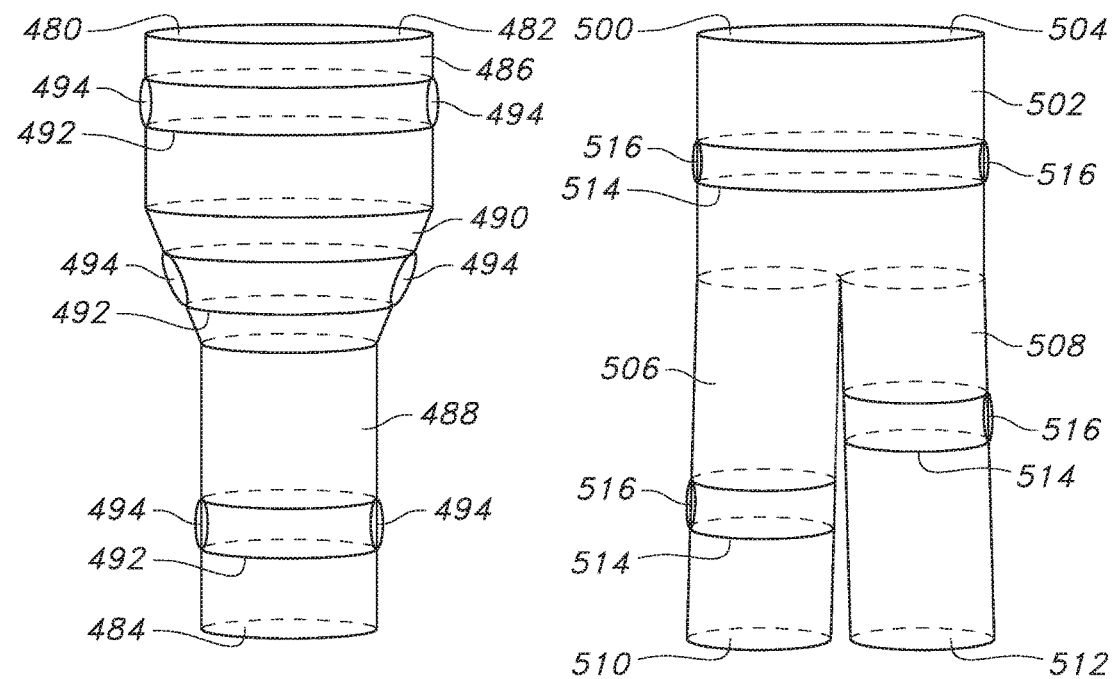

As depicted in FIG. 13B, integrally woven pouch openings 454, 456 may be disposed away from the woven edges 458, 460. As depicted in FIG. 13C, integrally woven graft 480 may have a first diameter at a first portion 486 near open end 482 and a second diameter, different from the first diameter, at a second graft portion 488 near open end 484 and a flared portion 490 integrally woven therein between. Any of the portions 486, 488, 490 may contain one or more circumferential pouches 492 having one or more openings 494. As depicted in FIG. 13D, integrally woven, bifurcated graft 500 main include a main body 502 having an open end 504 and two opposed legs 506, 508, each having an open end 510, 512. Any of the graft portions 502, 506, 509 may have one or more circumferential pouches 514 having one or more pouch openings 516.

An embodiment of the invention is directed to a method of making an integrally woven textile having a first end, a second end and a length therebetween, containing at least one longitudinal textile portion and at least one pouch, comprising: (a) weaving a longitudinal textile portion using a set of yarns; (b) weaving a first pouch with a slit opening therein integrally with the longitudinal textile portion from at least a portion of said set of yarns; (c) optionally repeating steps (a) and/or (b) from one to three times to integrally weave one or more additional segments with the longitudinal textile portion and the first pouch; and (d) threading an element through the slit opening of the pouch. In an embodiment thereof, the element is a radiopaque marker. In another embodiment, the element is nitinol wire.

Another embodiment is a method of making an integrally woven textile having a first end, a second end and a length therebetween, containing a base textile layer and at least one flap or pouch, comprising: weaving a base textile layer using a set of yarns; and weaving a pouch integrally with the base textile layer from at least a portion of said set of yarns. The yarns are made up of at least one set of weft yarns and at least one set of warp ends.

A further embodiment is an integrally woven graft comprising a first end, a second end and a length therebetween defining a longitudinal tubular graft portion having an inner wall and an outer wall and a lumen therethrough, said longitudinal tubular graft portion comprising a woven set of yarns, and at least one integrally formed pouch external to the lumen comprising at least a portion of said woven set of yarns. The longitudinal tubular graft portion and the pouch may have a common wall, optionally thereby forming a continuous tube from the first end to the second end of the graft.

A third embodiment relates to an integrally knitted textile having a first end, a second end and a length therebetween. The integrally knitted textile comprises a longitudinal textile portion knitted from a set of yarns, and at least one tab or pouch knitted from at least a portion of the same set of yarns and integrally knitted with the longitudinal textile portion. As such, the textile is made up of multiple segments. The textile may include one longitudinal textile portion or, in other embodiments, multiple segments of textile portions that may be joined by one or more integrally knitted pouches knitted there between. In one embodiment, the textile or tape may be knitted in the construction of single layer or double layer material. The textile may be constructed with two or more layers knitted together for a thicker or thinner and denser or less dense textile. In another embodiment, the process to knit a textile with integral pouches utilizes a single guide bar for the fabric layer, or two guide bars for the fabric layer, or 3 guide bars for the fabric layer, or four guide bars for the fabric layer, or as many guide bars to knit the fabric layer or pouches. The machine parameters or type of machine limits the maximum number of guide bars that may be used in the process of knitting a textile with integrally pouches.

A brief, but non-limiting, summary of the knitted structures in the below described figures are summarized below in Table A.

TABLE A

| FIGS.: | Layers Of Fabric Of Non-Pouched Portions | Guide Bar Threading | No. of Guide Bars* per Fabric Layer |
|---|---|---|---|
| 14 A, B, C | Two (no single layer of the textile tape or sheet is shown since guide bars are fully threaded) | Full | 2 |
| 14 D, E | One (element reference nos. 672 & 674) (element reference nos. 682 & 684) | Tape or sheet is full, pouch is partial (center zone) | 2 |
| 15 A-E | One (element reference nos. 720 & 724 or 792 & 786) | Tape or sheet is full, pouches are partial | 1 |
| 16 A-E | Two (no single layer of tape or sheet shown since guide bars are fully threaded) | Full | 1 |

*Optionally additional guide bars may be used to close openings pouches or to create center slits.

Figure 14A:
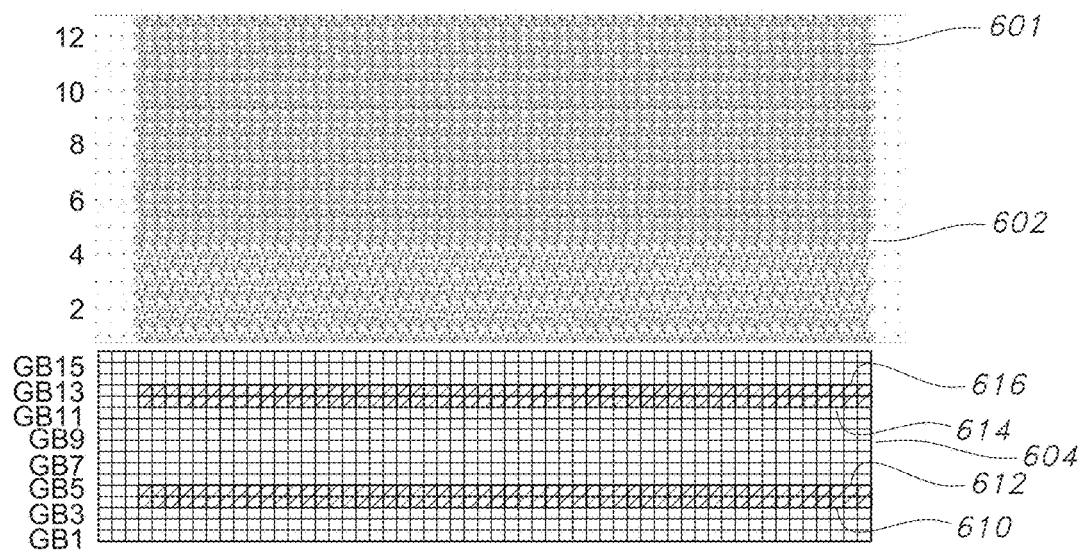
FIGS. 14A-14E are patterns and drawings of a partially and fully threaded knitted textile containing integrally knitted pouches.

FIG. 14A-14E show knit pattern and drawings of a knitted textile comprising integral knitted pouches throughout the textile. FIG. 14A is a knit pattern of lapping and threading diagram for one repeat section 601 for a knitted tape or flat sheet comprising integrally knitted tube pouches. The knit pattern 601 includes a loop and stitch pattern 602 and a threading diagram for guide bars 604. In one embodiment, shown in FIG. 14A, four guide bars (two guide bars per fabric layer), two guide bars partially threaded are utilized in the construction of the pouch and fully threaded guide bars for the construction of the tape, are fully and partially threaded. In this embodiment, the four guide bars utilized during this tube to tape knitting process are Guide Bar 4 (GB4) 610, Guide Bar 5 (GB5) 612, Guide Bar 12 (GB12) 614, Guide Bar 13 (GB13) 616 with the following stitch notation:

Guide Bar 4
1-2/1-1/1-0/1-1//*6
Guide Bar 5
1-0/1-1/1-2/1-1//*6
Guide Bar 12
1-0/1-2//*4+
1-1/1-0/1-1/1-2//*4
Guide Bar 13
1-0/1-2//*4+
1-0/1-2/1-1/1-0//*4

Figures 14B, 14C:
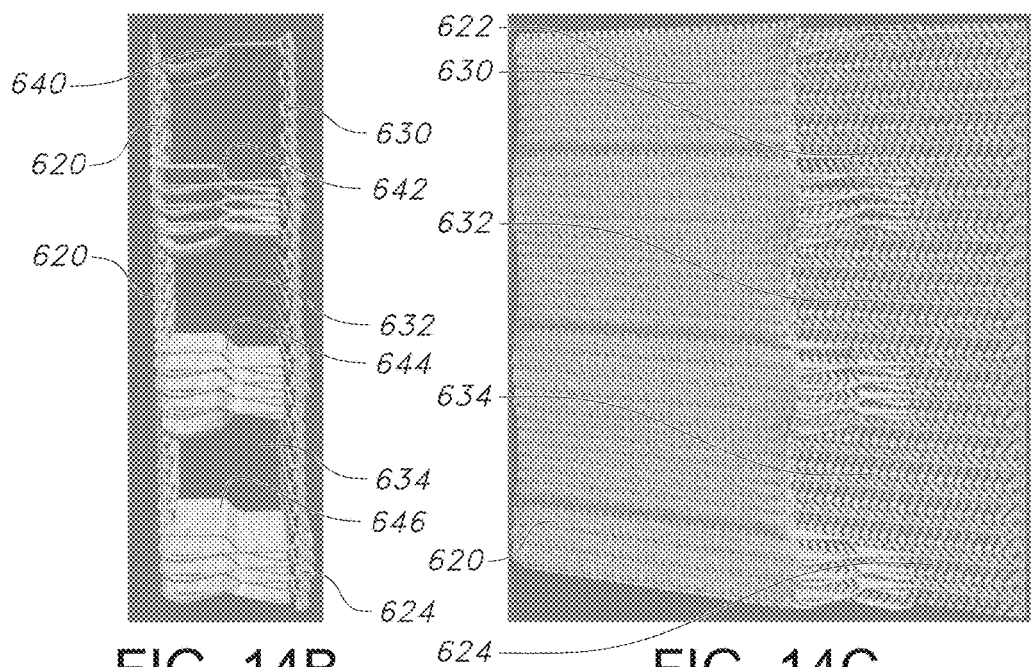

FIGS. 14B and 14C are drawings of the side cross section and angled cross section, respectively, of the knitted textile tape or sheet comprising integrally knitted pouches. FIG. 14B is a two dimensional drawing of 14A. FIG. 14B shows an integrally knitted double layer flat tape 620 having opposed ends layers 622, 624 and containing three tubular pouches 630, 632, 634, respectively. The tubular pouches 630, 632, and 634 are integrally knitted between the two opposing sides 622, 624 of the double layer flat tape 620 and separated by portions of integrally knitted warp yarns 640, 642, 644, and 646. FIG. 14C is a three dimension drawing of the angled cross section of the knitted double layer tape 620 comprising three integral pouches 630, 632, and 634 knitted between the opposing sides 622, 624 of the tape. The knit machine constructing or knitting the tape 620 with three tubular pouches 630, 632, 634 is fully threaded, shown in the center section of knit pattern 601.

Figure 14D:
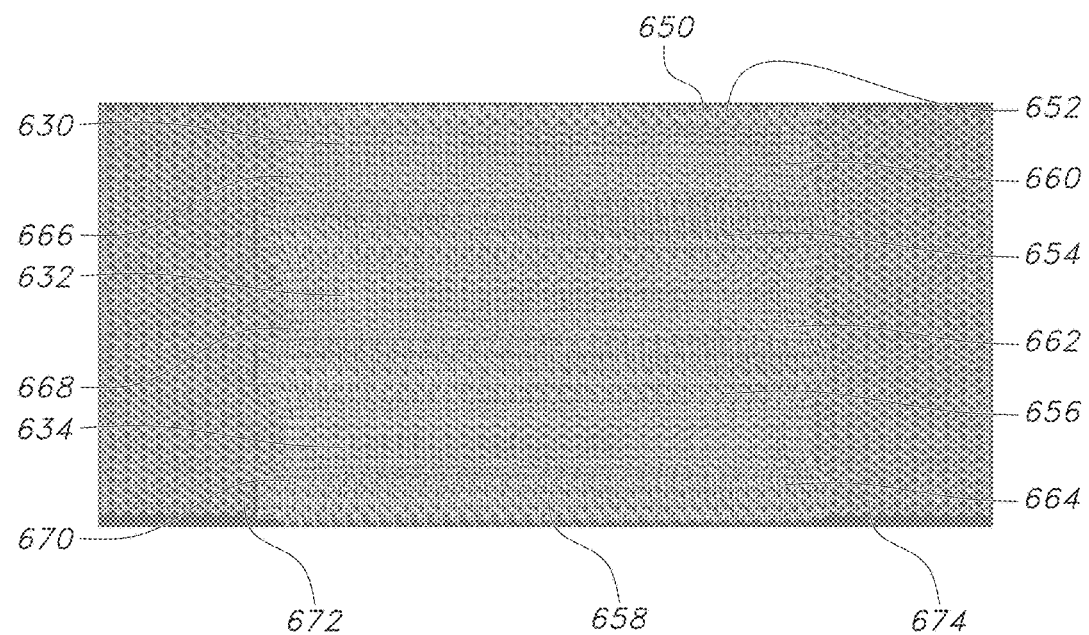

FIG. 14D is a two dimensional drawing of the front view of the knitted tape comprising integrally knitted pouches. Knitted tape 650 comprises three integrally knitted pouches 630, 632, and 634, each pouch having two sides 652, 654, 656, 658 and two slit openings 660 and 666, 662 and 668, and 664 and 670, respectively, and two non-pouch portions 672, 674. To knit each pouch, all guide bars are positioned together to knit the pouch sides 652, 654, 656, 658, and guide bars are separated at opposing sides to knit the tubular pouches 630, 632, and 634, shown in pattern 601.

Figure 14E:
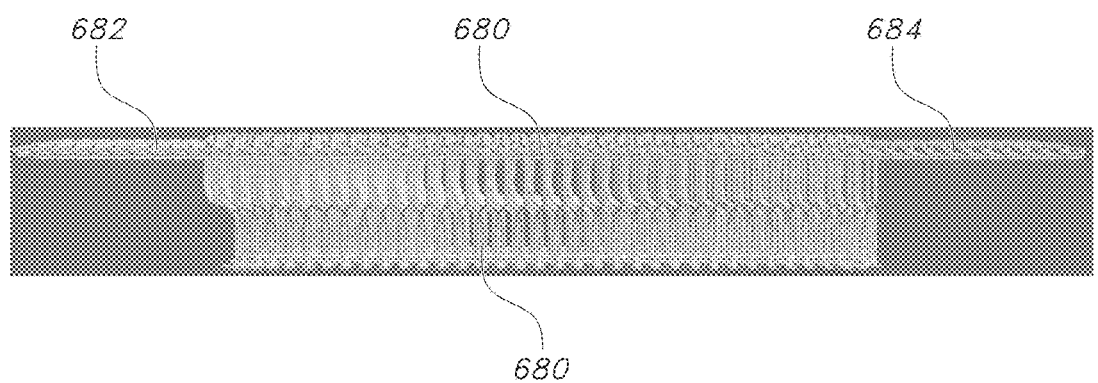

FIG. 14E is a bottom-up or top-down view drawing showing knitted textile 680 with single layer tape portions 682, 684 and double layer tape portion 686. The double layer tape portion or section contains integrally knitted pouches. The double layer of tape is not drawn to scale, in order to discern the layers. As depicted in FIGS. 14A and 14E, the guide bars are fully threaded to knit the single layer flat tape 682, 684 portions (not containing pouches) and partially threaded to knit the double layer tape with pouches 686, according to stitch notation and pattern 601.

Figure 15A:
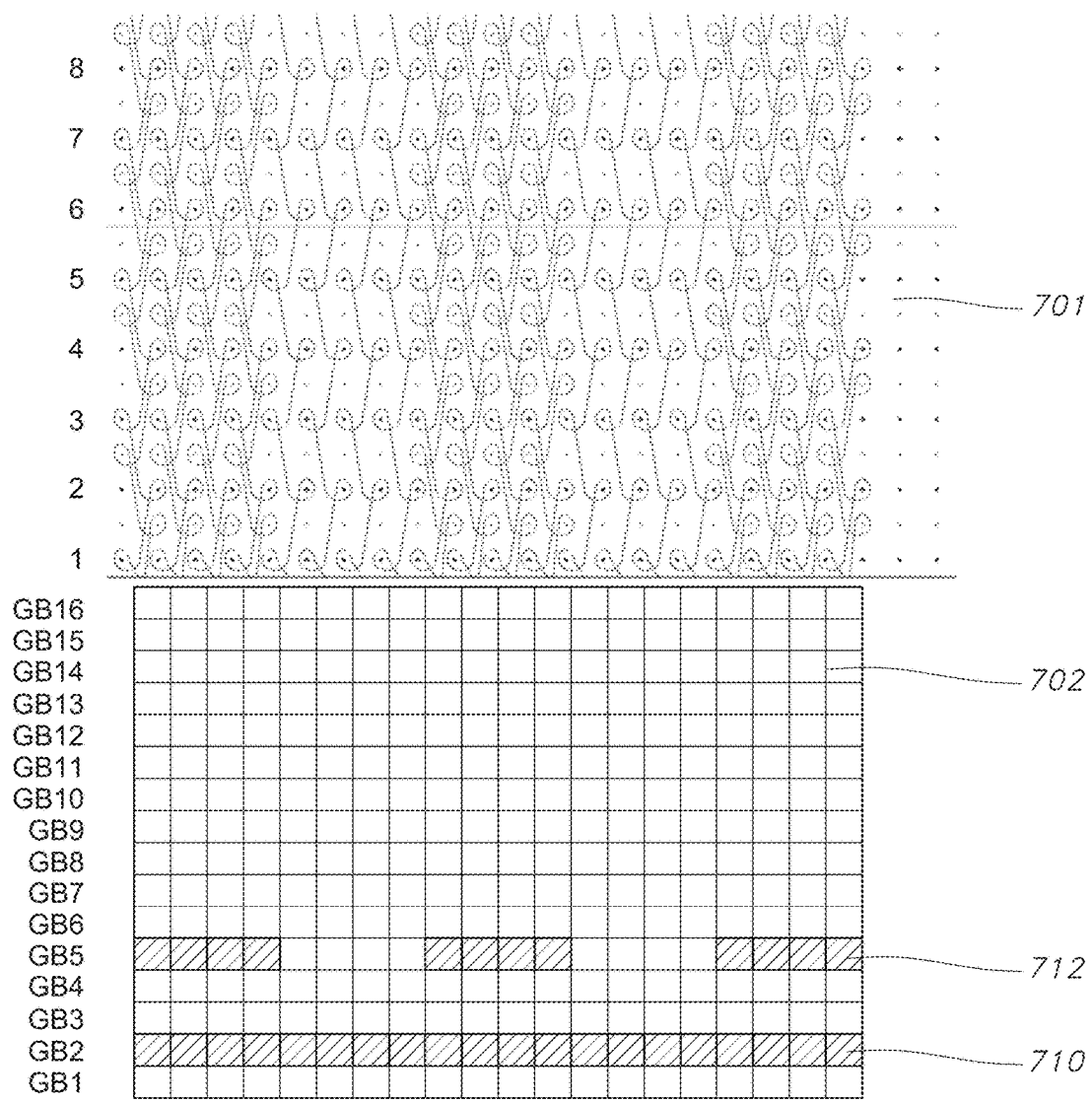
FIGS. 15A-15E are patterns and drawings of a partially threaded knitted textile containing integrally knitted pouches.

In another embodiment, a tape with integral pouches can be knitted using less yarn compared to FIGS. 14A-14E. In this embodiment, one guide bar per fabric layer is used to construct a knitted tape comprising integrally knitted tube pouches. FIGS. 15A-15E are knit patterns and drawings of a knitted textile comprising integral knitted pouches throughout the textile. As shown in FIG. 15A, the lapping and threading diagram for one repeat section 701 and a threading diagram for guide bars 702 for a single layer knitted tape comprising two integrally knitted tube pouches. In one embodiment, shown in FIG. 15A, one guide bar 710 is fully threaded in the construction of the tape, and a partially threaded guide bar 712 is utilized in the construction of two pouches. In this embodiment, the two guide bars utilized during this tube to tape knitting process are Guide Bar 2 (GB2) 710 and Guide Bar 5 (GB5) 712 with the following knit notation:

Guide Bar 2
1-2-1-1/1-0-1-1//*N+
0-1-0-0/0-0-0-1//*N
Guide Bar 5
1-1-1-0/1-1-1-2//*N+
1-1-1-0/1-0-1-1//*N

*N=is the designation for the number of repeats used depending on the length of the knit tape to pouch ratio.

Figures 15B, 15C:
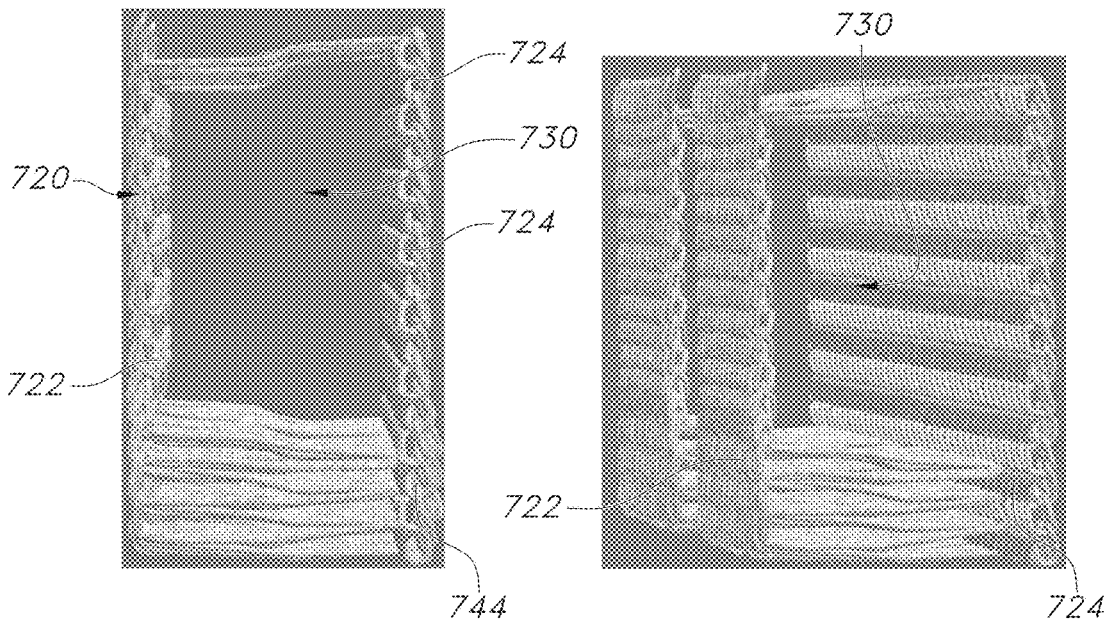

FIGS. 15B and 15C are drawings of the side cross section and angled cross section, respectively, of the double layer knitted textile tape comprising two integrally knitted pouches. FIG. 15B is a two dimensional drawing of a double layer knitted flat tape 720 having opposed layers 722, 724 containing a tubular pouch 730. The tubular pouch 730 is integrally knitted between the double layer flat tape sides 722,724 and end portions 742, 744. FIG. 15C is a three dimension drawing of the angled cross section of a knitted tape comprising two integral pouches 730 integrally with the double layers 722, 724 of the knitted tape.

Figure 15D:
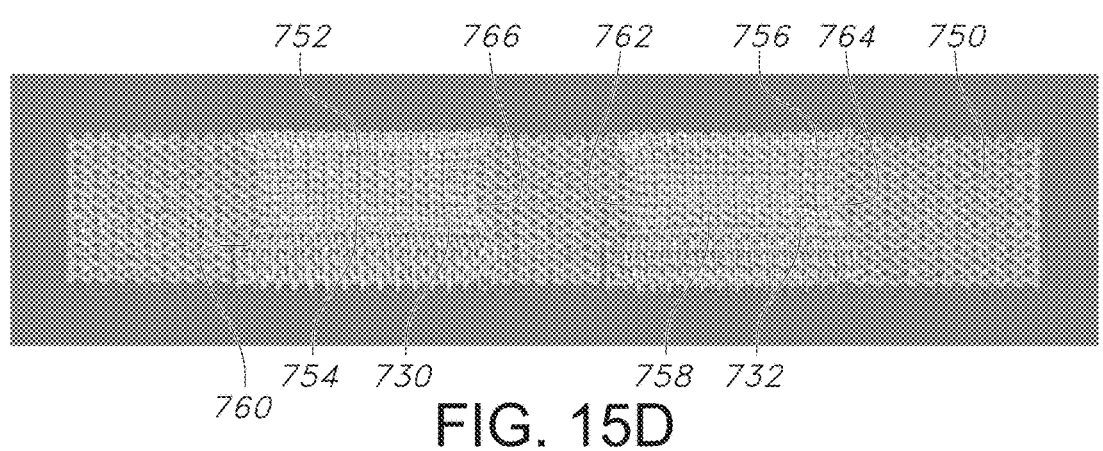
Figure 15E:
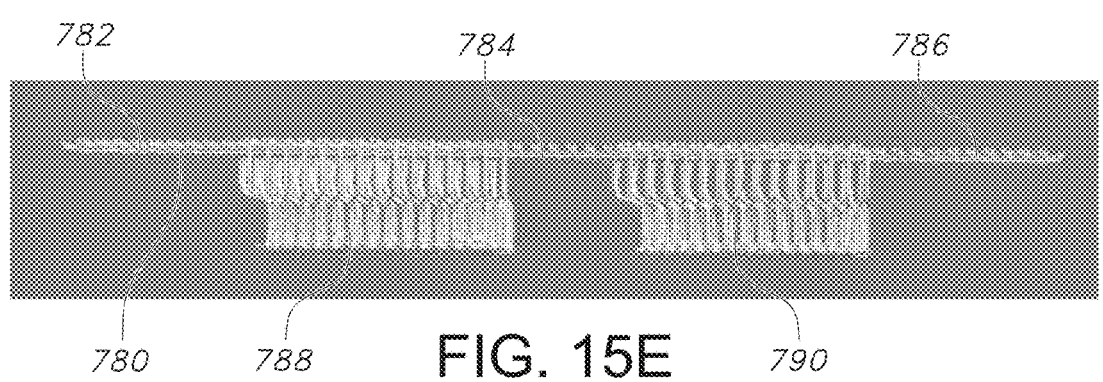

FIG. 15D is a two dimensional drawing of the front view of the knitted tape comprising integrally knitted pouches. Knit tape 750 comprises two integrally knitted pouches 730 and 732, each pouch having two sides 752, 754, and 756, 758, respectively, and two open slits 760, 766 and 762, 764, respectively. FIG. 14E is a bottom-up or top-down view drawing showing a knitted textile or tape 780 with knitted pouches 788 and 790 integrally knitted within two layers of the tape, and a single layer tape portions 782, 784 and 786. Pouches 788, 790 are constructed by separating or distancing the two guide bars to create a void area or open area between two knitting layers. As shown in FIG. 15E, guide bars are partially threaded to construct the single layer flat tape portions 782, 784 and 786 and guide bars are fully threaded and positioned away from one another to construct the pouches 788, 790. The area, dimensions and scale of the pouches and tape portions are not to scale, in order to discern the layers. As depicted in FIG. 15E, the non-pouch single layer flat tape 782, 784 and 786 portions and pouches 788,790 are knitted according to stitch notation 701, as in FIG. 15A.

Figure 16A:
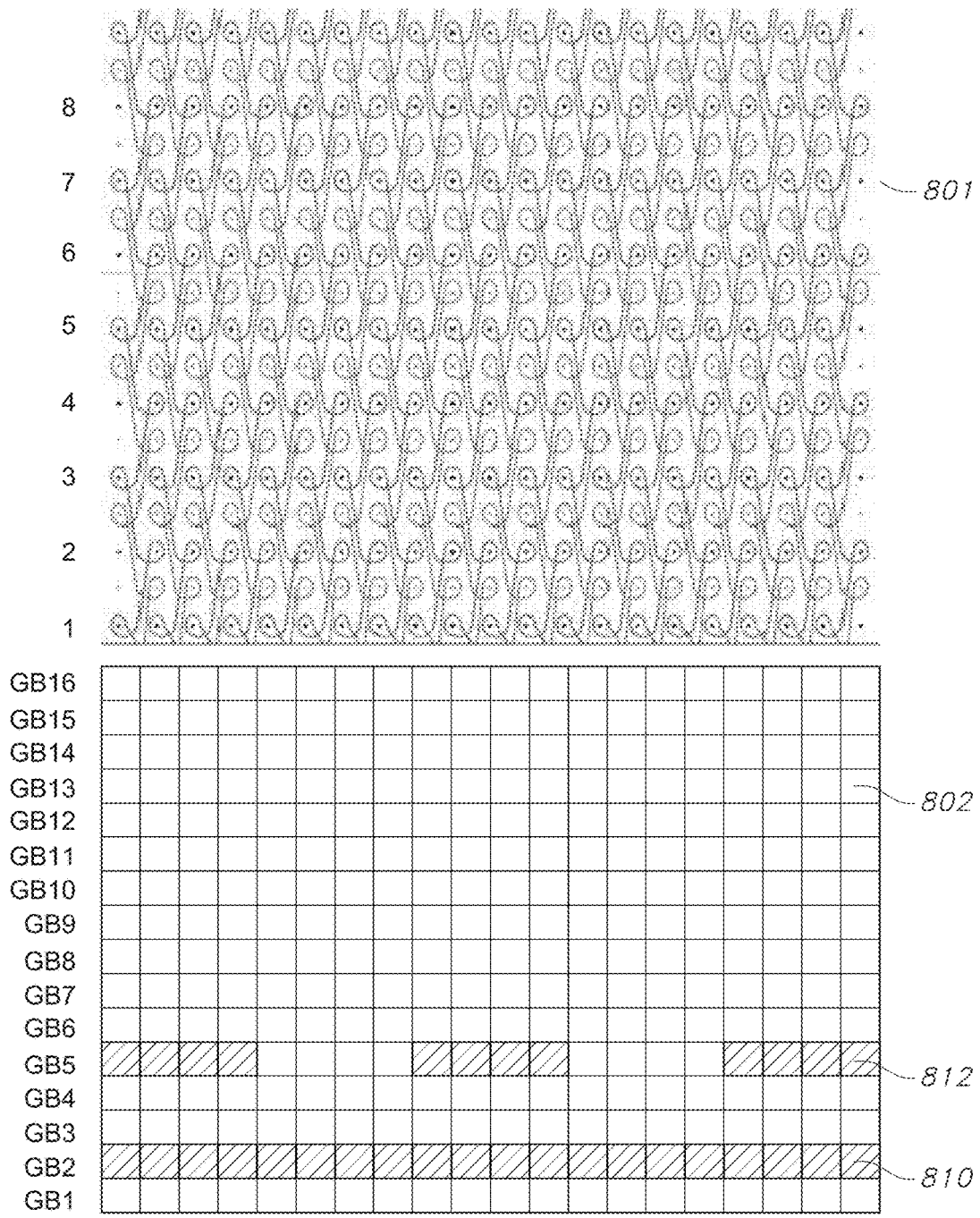
FIGS. 16A-16E are patterns and drawings of a fully threaded knitted textile containing integrally knitted pouches.

Further, in another embodiment, all guide bars used to construct a knitted tape comprising integrally knitted tube pouches are fully threaded with yarn or fabric. As shown in FIG. 16A, the lapping diagram 801 and the guide bar threading diagram 802 are utilized for a knitted tape comprising integrally knitted tube pouches. Shown in FIG. 16A, two guide bars are fully threaded to knit the double layer flat tape and tube pouches. In this embodiment, the two guide bars utilized during this tube to tape knitting process are Guide Bar 2 (GB2) 810 and Guide Bar 5 (GB5) 812 with the following knit notation:

Guide Bar 2
1-2-1-1/1-0-1-1//*N+
0-1-0-0/0-0-0-1//*N
Guide Bar 5
1-1-1-0/1-1-1-2//*N+
1-1-1-0/1-0-1-1//*N

*N=the designation for the number of repeats used depending on the length of the knit tape to pouch ratio.

Figure 16B:
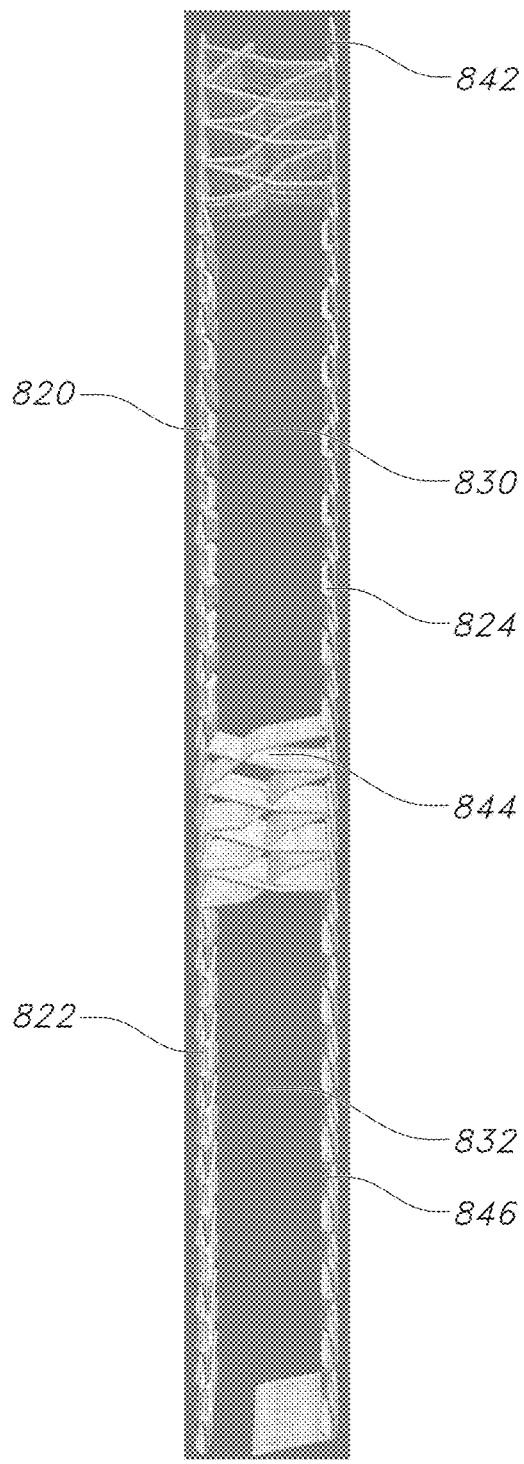
Figure 16C:
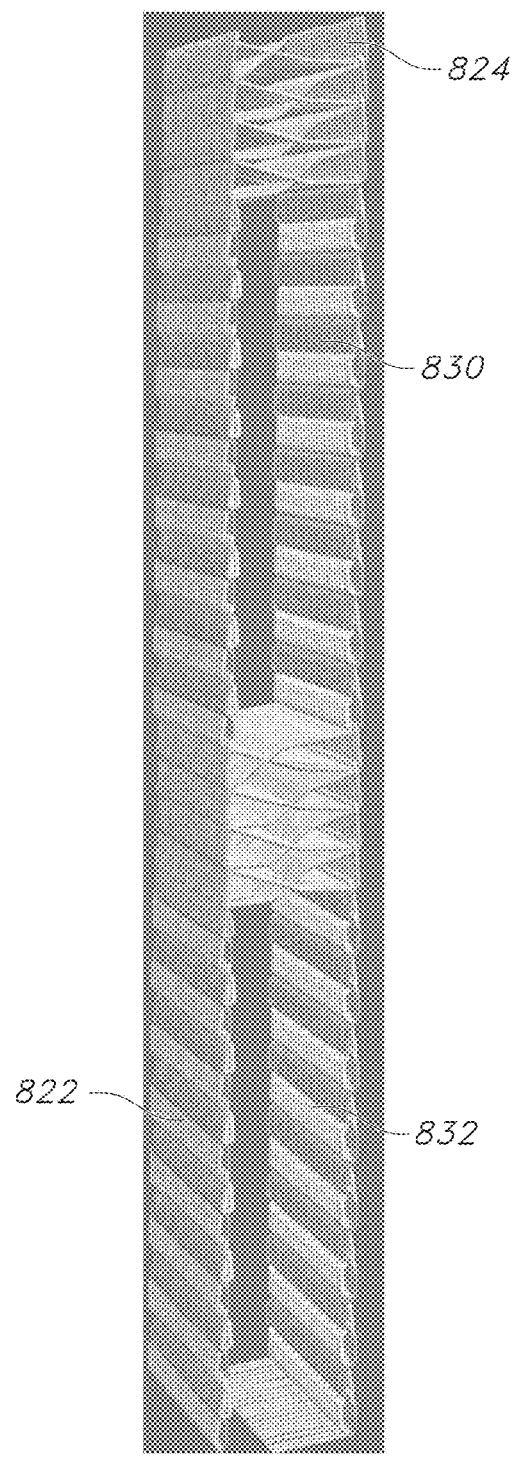

FIGS. 16B and 16C are drawings of the side cross section and angled cross section, respectively, of the knitted textile tape comprising integrally knitted pouches or tabs. FIG. 16B is a two dimensional drawing of an integrally knitted double flat tape 820 having opposed ends layers 822, 824 and containing pouch 830 and tab or extended textile portion 832. The pouch 830 and flap or tab 832 are integrally knitted from the opposing flat tape sides 824 or 820. Pouch 830 is fully closed and integrally connected to the flat tape at four sides 822, 824, 842, and 844, (or portions of integrally knitted warp yarns representing sides 842 and 844). Whereas, the tab or extended textile portion 832 is open or connected to the flat tape at three sides 822, 824, and 844 (or portions of integrally knitted warp yarns representing side 844) of tab with one side 846 open or not connected integrally with the flat tape. FIG. 16C is a three dimensional drawing of the angled cross section of a double layer knitted tape comprising integral pouches or tabs 830, 832 extending from the flat tape layer 824. The side of the knit machine constructing or knitting the panel or tape 824 is fully threaded and the machine constructing or knitting the pouch 830 and tab 832 is fully threaded with yarn or other fibers.

Figure 16D:
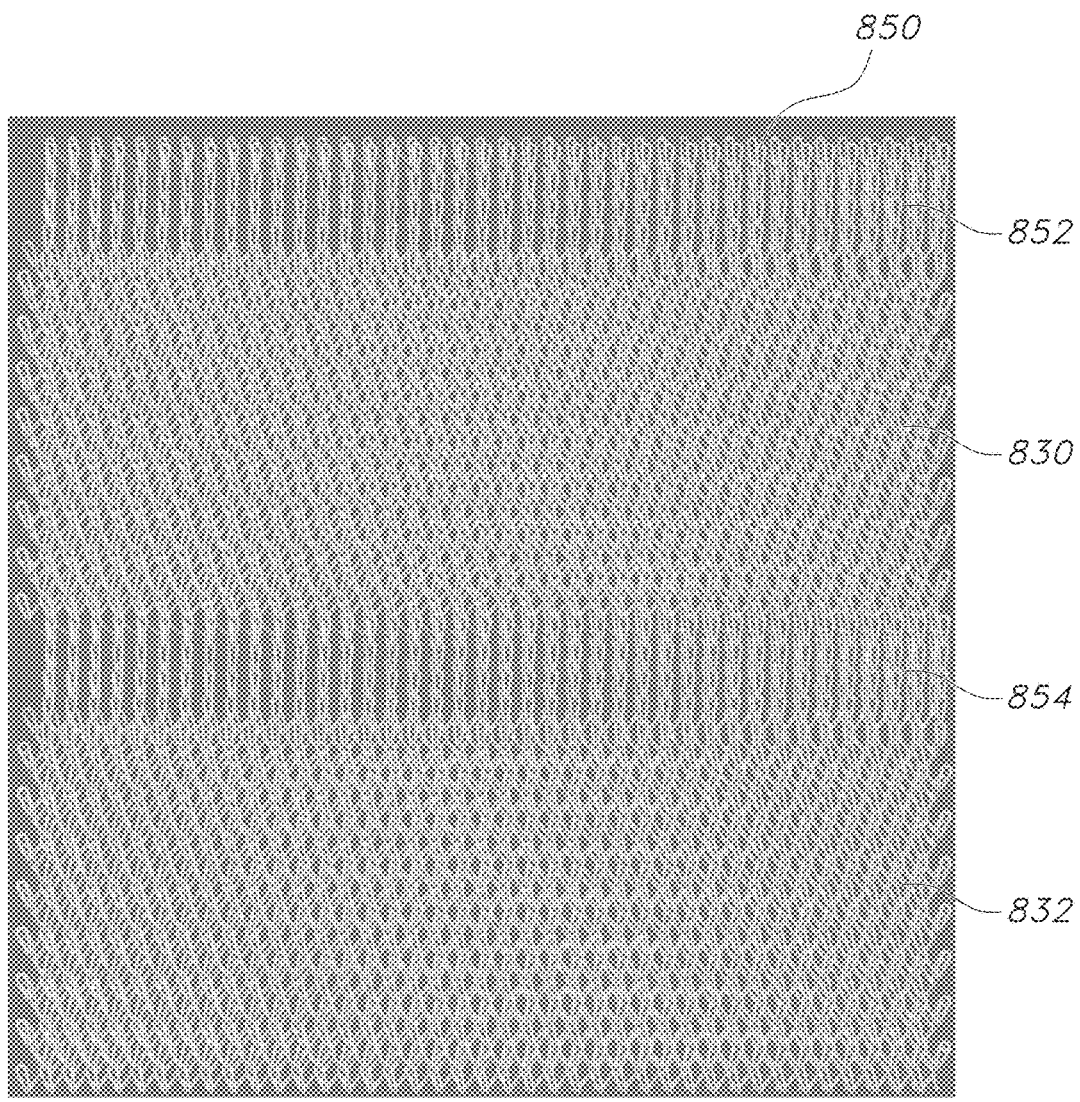
Figure 16E:
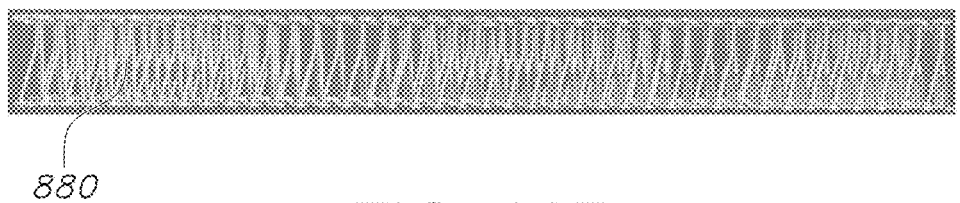

FIG. 16D is a two dimensional drawing of the front view of the double layer knitted tape comprising integrally knitted pouches. Knit tape 850 comprises two integrally knitted pouches 830, 832. The integrally knitted pouch 830 has two closed or attached sides 852 and 854. If pattern 801, in FIG. 16A, is repeated, pouch 832 would also have two closed or attached sides. In this embodiment, the pouches are not knitted closed, if additional partially threaded guide bars were added they would be closed on all four sides and would not have open slits. FIG. 16E is a top-down or bottom-up view drawing showing knitted textile 880 with integrally knitted pouches (Pouches cannot be visualize in FIG. 16E due to the double layer construction of the tape throughout.). As depicted in FIG. 16E, the double layer knitted tape with integral pouches 880 is knitted according to knit pattern 801, as in FIG. 16A, with all guide bars fully threaded.

In an embodiment, a method of making an integrally knitted textile having a first end, a second end and a length therebetween, containing at least one longitudinal textile portion and at least one pouch or tab or sac, comprising: (a) knitting a longitudinal textile portion using a set of yarns; (b) knitting a first pouch or tab or sac with a slit opening therein integrally with the longitudinal textile portion from at least a portion of said set of yarns; (c) optionally repeating steps (a) and/or (b) from one to three times to integrally knit one or more additional segments with the longitudinal textile portion and the first pouch or tab or sac; and (d) threading an element through the slit opening of the pouch or tab or sac. In an embodiment thereof, the element is a radiopaque marker. In another embodiment, the element is nitinol wire.

As those skilled in the art will appreciate, numerous changes and modifications may be made to the embodiments described herein, without departing from the spirit of the disclosure. The base textile and pouch or pouches can be formed using traditional loop structures or lapping movements such as a 1 and 1 lapping movement, 2 and 1 lapping, pillar or a combination of lapping movements known to those skilled in the art such as tricot, locknit, satin, atlas, etc. but are either transferred to the adjacent needle bar to close a pouch or left knitting on separate needle bars to keep the pouch open. Longitudinal or diagonal pouches are formed by the use of fully or partially threaded guide bars. An atlas stitch using fully or partially threaded guide bars can create a diagonal pouch in the area that is not threaded with the joining yarns thus creating a pouch. It is intended that all such variations fall within the scope of the invention. For example, Raz S. (1987) Warp Knitting Production. Charlottesville, Va.: Melliand Textilberichte, which is incorporated by reference herein in its entirety, teaches knitting processes, machine methods and guide bar configurations for traditional textile constructions. These methods and processes may be used as presented by the reference or modified for specific embodiments described herein.

A sixth embodiment is a method of making an integrally woven or knitted flat textile having a first end, a second end and a length therebetween, containing a base textile layer and at least one pouch, tab or extended textile portion, comprising: weaving or knitting a base textile layer using a set of yarns; and weaving or knitting a pouch or tab integrally with the base textile layer from at least a portion of said set of yarns, then disconnecting one or more integrally connected sides. The yarns are made up of at least one set of weft yarns and at least one set of warp ends.

Figure 17A:
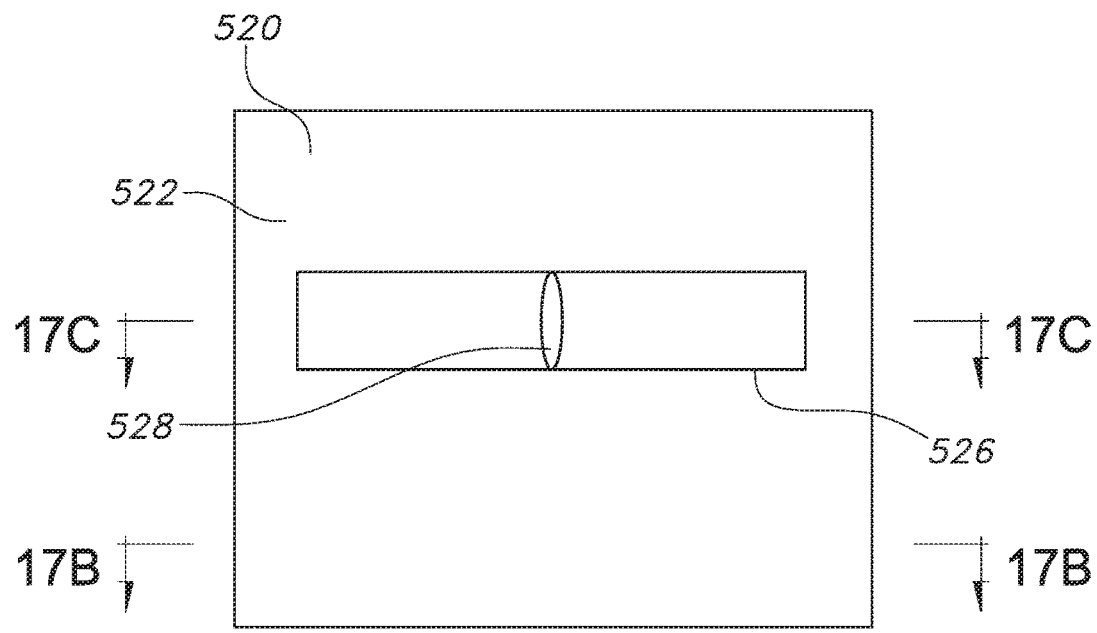
FIGS. 17A-17C are drawings of integrally woven or knitted flat textile containing a pouch with a slit opening at the center of the pouch.
Figure 17B:
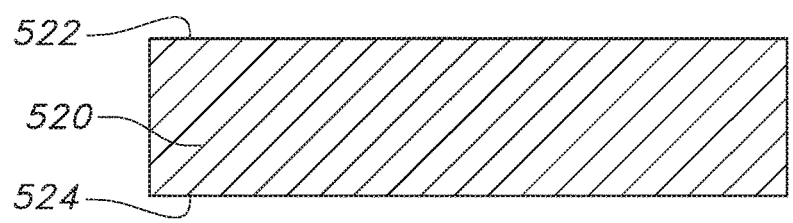
Figure 17C:
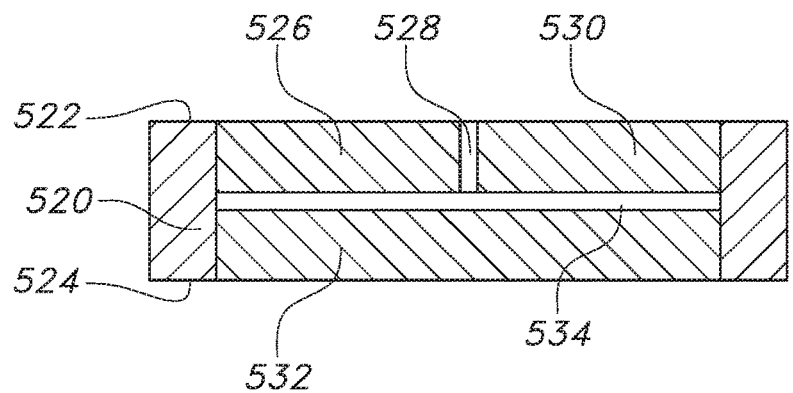

FIG. 17A depicts a textile sheet 520 having a pouch 526 with a pouch opening 528. The textile sheet 520 may be a unitary knitted or woven textile. As depicted in FIG. 17B, cross sectional view of textile sheet at 17B-17B axis of FIG. 17A, the textile sheet 520 may be a single layered textile sheet having a top portion 522 and a bottom portion 524. In another embodiment, the textile sheet may be composed of multiple layers (not shown) woven together to create a single layer. As depicted in FIG. 17C, cross sectional view of textile sheet at 17C-17C axis of FIG. 17A, pouch 526 includes an upper portion 530 and a lower portion 532 having a pouch cavity 534 therein between. The textile sheet may be a woven sheet or a knitted sheet with the pouch integrally formed, e.g. integrally woven or integrally knitted.

Figure 18A:
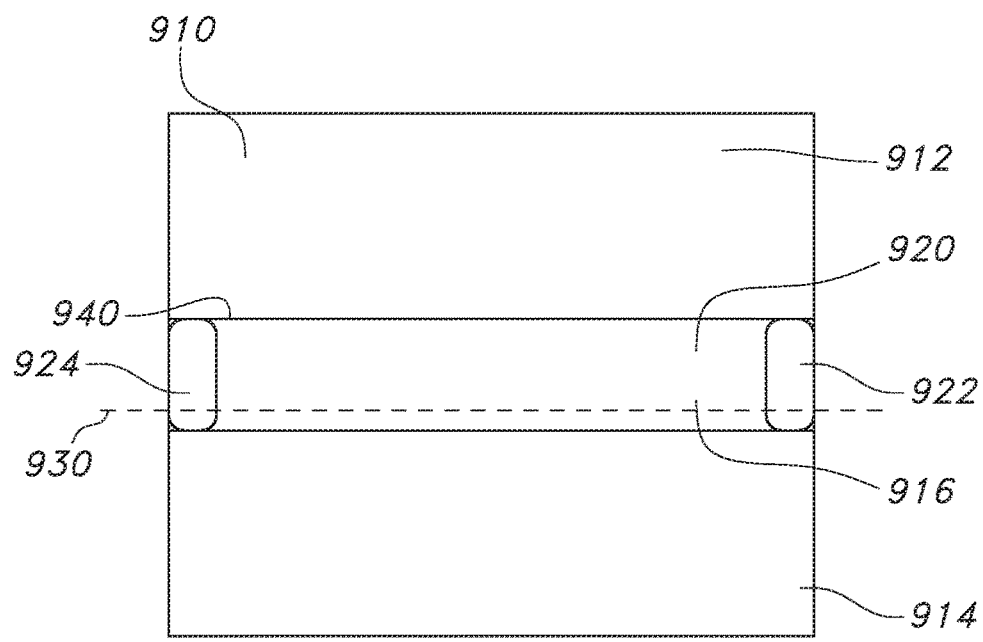
FIGS. 18A-18B are two dimensional drawings of a tab, flap or extended textile segment on a flat textile.
Figure 18B:
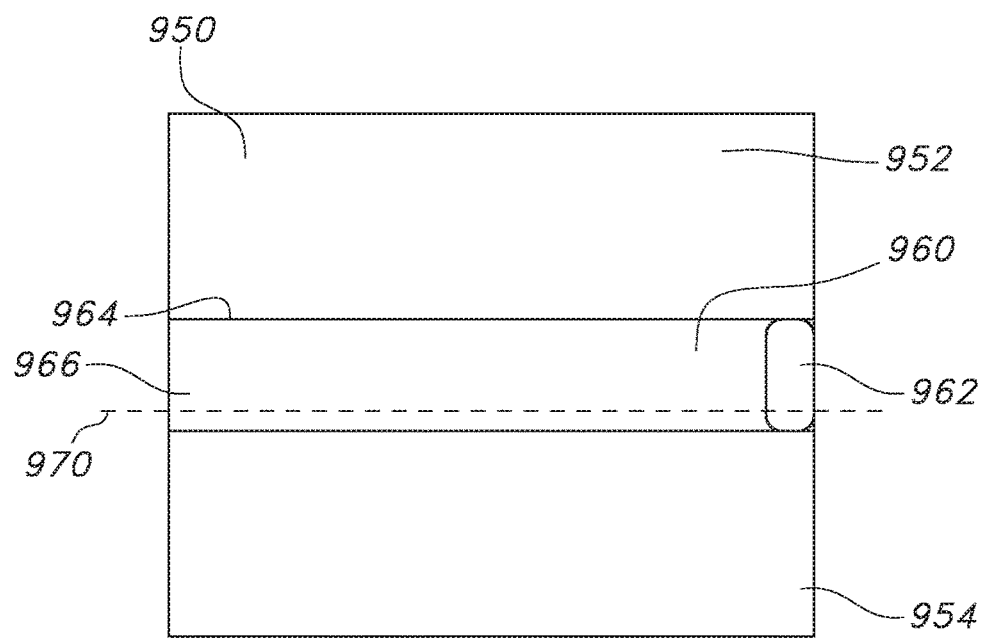

In another embodiment, a woven or knitted flat textile with an integrally woven or knitted tab, flab or extended textile portion is shown in FIGS. 18A and 18B. FIG. 18A is a two dimensional drawing of a woven or knitted flat textile 910 with two woven or knitted flat portions 912 and 914 and one integrally woven or knitted tab 920. In one embodiment, shown in FIG. 18A, the woven or knitted tab is integrally connected at one side 940 of the tab 920. Tab 920 is created by first weaving or knitting a pouch 916 with two open ends or slits 922 and 924, then disconnecting (i.e. cutting) one side of the pouch. In one embodiment, the pouch 916 may be disconnected at cut line 930. FIG. 18B is a two dimensional drawing with a tab 960 connected at two sides 964, 966 and open at two side 962, 970. The cut may be positioned substantially parallel or perpendicular to the longitudinal, circumferential or diagonal axis of the pouch. Additionally, the cut is not limited to a straight line.

In order to create a pouch, the weave pattern must be altered from the pattern used to weave the longitudinal tubular graft portion. In an embodiment, Shuttle 1 is used to the weave the longitudinal tubular graft portions and inner tubular walls of the pouches, Shuttle 2 is used to make the exterior side (or outer tubular wall) of the first pouch, and Shuttle 3 is used to make the exterior side (or outer tubular wall) of the second pouch. In an embodiment, the longitudinal tubular graft portion is woven according to the plain weave pattern of FIG. 2 and the following changes are made to the plain weave pattern to make the weave pattern for the pouches that are circumferentially or diagonally positioned about the graft:

Change the pattern repeat to cover 8 warp ends and 8 picks. Four warp ends and 4 picks correspond with Shuttle 1 and the other 4 warp ends and 4 picks correspond with Shuttles 2 and 3. In order to create a slit opening that provides access to the pouch, the repeat for Shuttle 2 must be split in half by making it sandwich Shuttle 1's pattern (2 picks on either side of Shuttle 1's 4 pick repeat). The order of the weaving repeat is as follows:
  i. Picks 1-2: Shuttle 2 (Top/Top);
  ii. Picks 3-6: Shuttle 1 (Top/Bottom/Top/Bottom);
  iii. Picks 7-8: Shuttle 2 or Shuttle 3 (Bottom/Bottom).

Whenever Shuttle 1 is weaving, the warp end for Shuttles 2 and 3 must be kept out of the way and vice versa. Whether the ends are raised or lowered depends on which of the inner or outer tubular walls they are being used to create.

Shuttle 1 and Shuttle 3 are started on one side (such as the right side) of the weaving apparatus (e.g., a loom). Shuttle 2 is started on the other side (here, the left side) of the weaving apparatus.

Shuttle 3 is used in the same manner as Shuttle 2, but in weaving the other of the two pouches of the graft in order to weave the slit opening in the opposite side of the pouches (i.e., 180 degrees offset).

Selecting which warp ends to weave in each tubular wall of the pouch assures that the pouch has an open inner tubular space through which an element, such as a radiopaque wire, may be threaded or housed. Changing the weave pattern to an 8 warp end/8 pick repeat allows specific ends and picks to correspond to each tubular wall of the pouch. Four warp ends and picks will be used to weave the inner tubular wall of the pouch and 4 warp ends and picks will be used to weave the outer tubular wall (exterior side) of the pouch. If the pattern is not changed to cover 8 ends and 8 picks, the ends would be woven into the tubular walls creating a tight spaced fabric that has the tubular walls woven together. That is, there would be no opening through which an element might be thread.

Selecting the side on which each shuttle starts weaving dictates on which side the slit opening will be woven into the outer tubular wall. Shuttle 1 and Shuttle 2 must start on opposite sides so that the weft yarns do not get trapped. Shuttle 3 must start on the opposite side of Shuttle 2 so the slit openings are on opposite sides of the graft (i.e., offset by 180 degrees).

The sequence of weaving the pouch is important. For example, the outer tubular walls of the first and second pouches cannot be woven (to completion) with Shuttles 2 and 3 before the inner tubular wall is woven using Shuttle 1 or else there will be no access to the inside of the graft in order to weave those inner portions.

Further, if the weave pattern is not converted so that the warp ends are out of the way when not being used in weaving the tubular wall, then the pouch or even the entire graft will be woven shut, eliminating the opening in the pouch design. More specifically, if the warp ends of the top inner tubular wall (FIG. 6) are being woven and the warp ends of the top outer tubular wall (FIG. 6) are not being woven, those ends need to be raised up so that they are not accidentally woven into the tube. If this happens, the tube will be woven shut.

FIGS. 19-22 are cross sectional views of how the warp ends look when each of the four tubular walls of the pouch are being woven. For each of these figures:
  Numeral 1 denotes the warp ends used to weave the top outer tubular wall (FIG. 6) of the pouch;
  Numeral 2 denotes the warp ends used to weave the top inner tubular wall (FIG. 6) of the pouch;
  Numeral 3 denotes the warp ends used to weave the bottom inner tubular wall (FIG. 6) of the pouch; and
  Numeral 4 denotes the warp ends used to weave the bottom outer tubular wall (FIG. 6) of the pouch.

Figure 19:
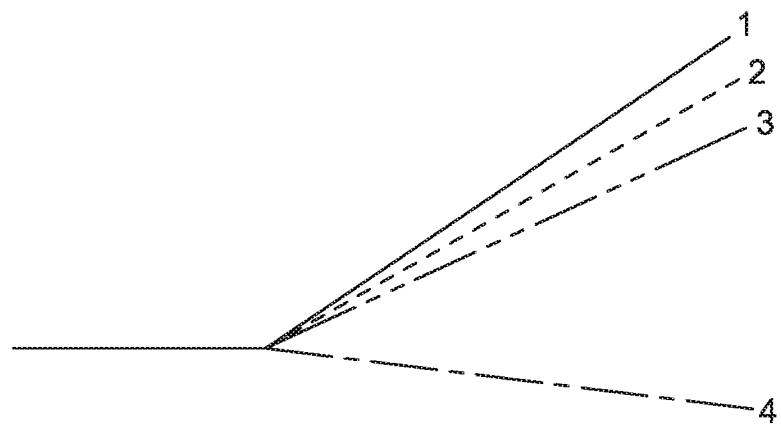
FIGS. 19 through 22 depict cross-sectional configurations of the 4 sets of warp ends used when weaving a circumferential pouch.
Figure 20:
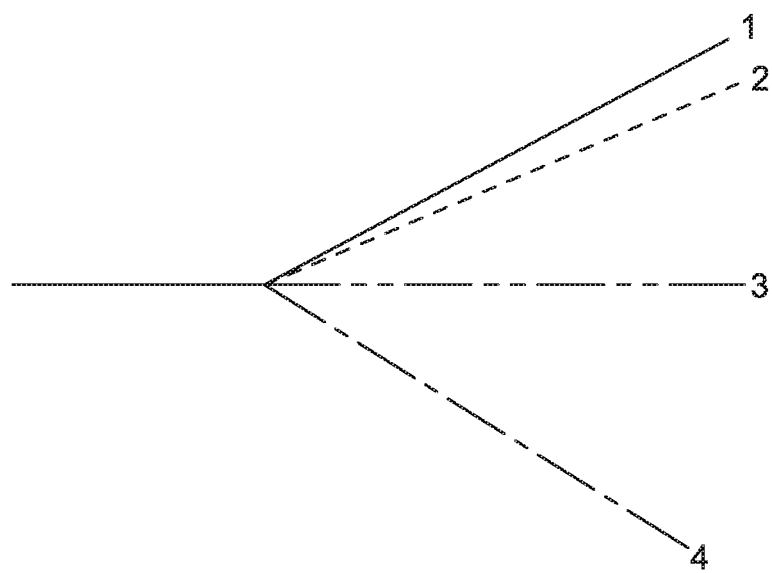
Figure 21:
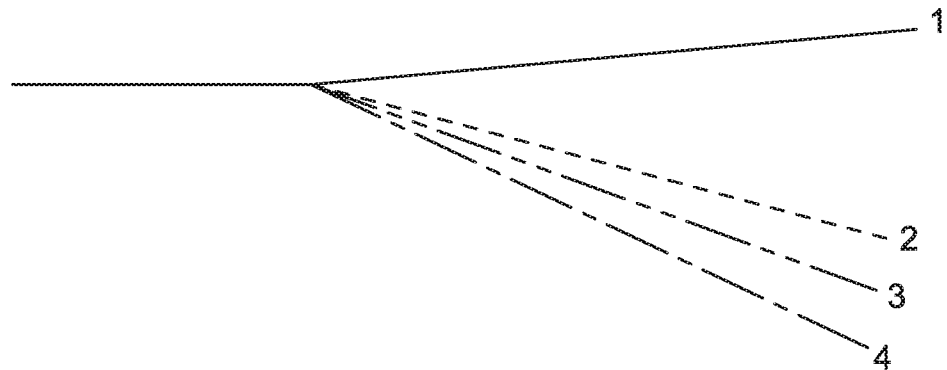
Figure 22:
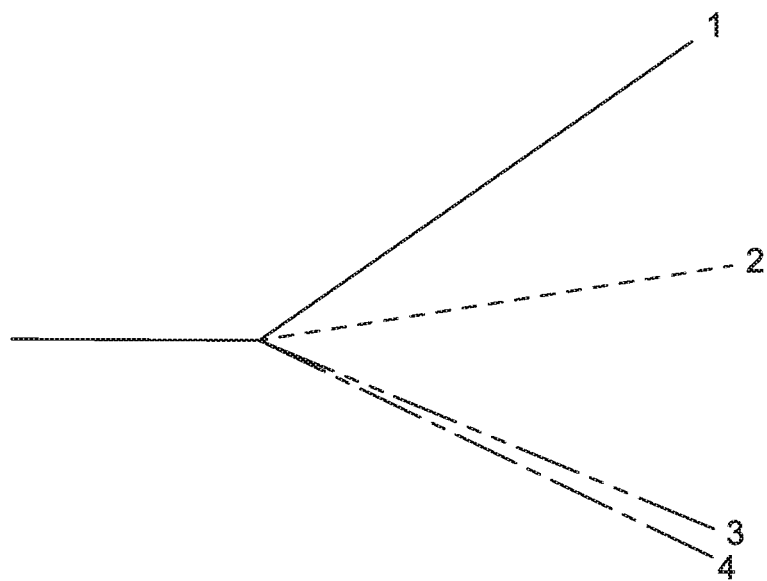

FIG. 19 is a cross-sectional view of the spacing of the warp ends when the bottom outer tubular wall is being woven. As shown, the warp ends used to weave the bottom outer tubular wall (4) are separated from the other ends (1-3), which are raised to be out of the way. FIG. 20 is view of the spacing of the warp ends when the bottom inner tubular wall is being woven. As shown, the warp ends 1 and 2 are raised and warp ends 4 are lowered to not interfere with the weaving of warp ends 3. FIG. 21 is view of the spacing of the warp ends when the top outer tubular wall is being woven. As shown, the warp ends 2-4 are lowered to not interfere with the weaving of warp ends 1. FIG. 22 is view of the spacing of the warp ends when the top inner tubular wall is being woven. As shown, the warp ends 3 and 4 are lowered and warp ends 1 are raised to not interfere with the weaving of warp ends 2.

Using the weave patterns substantially shown in FIGS. 2 and 3, it has been found that weaving a pouch without a slit opening on one side of the outer tubular wall of the pouch that is circumferentially positioned about the graft limits access to the inside of the pouch. Thus, an integrally woven graft with a longitudinal tubular graft portion and at least one pouch using these weave patterns also include a slit opening in each pouch. If the slit opening is not in the outer tubular wall of the graft, then there will be no access to the pouch and the picks will close the pouch on the opposite side.

The fabric density of the pouch (i.e., picks per inch) may be the same or different than the fabric density of the longitudinal tubular graft portion. In an embodiment, the picks per inch are doubled when weaving the pouch to maintain a fabric density in the pouch that is similar or equivalent to the longitudinal tubular graft portion of the graft.

In an embodiment, a continuous tube from the first end of the graft to the second end of the graft is woven via the continuous interwoven set of yarns of the longitudinal tubular graft portion and inner tubular wall of the pouch. In an embodiment thereof, both the set of warp end yarns and the set of weft yarns are the same throughout the continuous tube of the graft.

The integrally woven graft of the disclosure can be made in various sizes, densities, shapes, etc. just as any graft known in the art may be, optionally, with the weave or knit patterns as described herein.

As those skilled in the art will appreciate, numerous changes and modifications may be made to the embodiments described herein, without departing from the spirit of the disclosure. It is intended that all such variations fall within the scope of the invention.

What is claimed:

1. An integrally woven or knitted textile having a first end, a second end and a length there between, comprising:
    at least one longitudinal textile portion woven or knitted from a set of yarns; and
    at least one pouch or flap woven or knitted from at least a portion of said set of yarns and integrally woven or knitted with the longitudinal textile portion;
    wherein, if integrally woven, the set of yarns comprises at least one set of warp yarns or ends and at least one set of weft yarns or picks;
    wherein, if integrally knitted, the set of yarns comprises at least one set of wale yarns and at least one set of course yarns;
    wherein the at least one pouch is a first pouch having an outer wall, an inner tubular wall and an open inner space, positioned near the first end of the textile;
    wherein the first pouch has a slit opening positioned parallel to a longitudinal axis of the textile; and
    wherein the slit opening is woven or knitted in the outer wall of the first pouch and extends across the first pouch.

2. The textile of claim 1, comprising a second pouch having an outer wall, an inner wall and an open inner tubular space, near the second end of the textile.

3. The textile of claim 2, wherein each pouch has a slit opening positioned parallel to a longitudinal axis of the textile.

4. The textile of claim 3, wherein the slit opening in the first pouch and the slit opening in the second pouch are woven in the outer tubular wall of each of the pouches and extend across each of the pouches.

5. The textile of claim 4, wherein the slit opening in the first pouch is offset 180 degrees from the slit opening in the second pouch.

6. The textile of claim 2, wherein the at least one textile portion is woven from a first set of weft yarns, the first pouch is woven from at least a portion of the first set of weft yarns and a second set of weft yarns, and the second pouch is woven from at least a portion of the first set of weft yarns and either the second set of weft yarns or a third set of weft yarns.

7. The textile of claim 1, wherein the textile is a longitudinal tubular graft.

8. The textile of claim 7, wherein a cross-sectional view of the longitudinal tubular graft through the pouch has 4 layers of woven material.

9. The textile of claim 7, wherein the at least one pouch is circumferentially disposed about the longitudinal tubular graft.

10. The textile of claim 7, wherein the longitudinal tubular graft portion is continuous with an inner tubular wall of the pouch forming a continuous tube, and wherein the continuous tube extends from the first end of the graft to the second end of the longitudinal tubular graft.

11. The textile of claim 1, wherein the textile does not contain a seam between the pouch and the longitudinal textile portion.

12. The textile of claim 1, wherein an element is disposed within the pouch.

13. The textile of claim 12, wherein the element is a metal wire.

14. The textile of claim 1, wherein the yarns are resorbable or non-absorbable, and wherein the yarns are selected from the group consisting of a natural material, a synthetic material, a metal, and any combination thereof.

15. The textile of claim 1, wherein the at least one textile portion and the at least one pouch are woven from the same set of warp ends.

16. The textile of claim 1, wherein the at least one textile portion is woven from a first set of warp ends and the at least one pouch is woven from a portion of the first set of warp ends and at least one additional set of warp ends.

17. The textile of claim 1, wherein the at least one textile portion is woven from a first set of weft yarns and the at least one pouch is woven from at least a portion of the first set of weft yarns and at least one additional set of weft yarns.

18. The textile of claim 17, wherein a material of the first set of weft yarns is different from a material of the at least one additional set of weft yarns.

19. An integrally woven or knitted textile having a first end, a second end and a length there between, comprising:
    at least one longitudinal textile portion woven or knitted from a set of yarns; and
    at least one pouch or flap woven or knitted from at least a portion of said set of yarns and integrally woven or knitted with the longitudinal textile portion;
    wherein, if integrally woven, the set of yarns comprises at least one set of warp yarns or ends and at least one set of weft yarns or picks;
    wherein, if integrally knitted, the set of yarns comprises at least one set of wale yarns and at least one set of course yarns;
    wherein the at least one pouch is a first pouch having an outer wall, an inner tubular wall and an open inner space, positioned near the first end of the textile;
    a second pouch having an outer wall, an inner wall and an open inner tubular space, near the second end of the textile;
    wherein each pouch has a slit opening positioned parallel to a longitudinal axis of the textile; and
    wherein the slit opening in the first pouch and the slit opening in the second pouch are woven or knitted in the outer tubular wall of each of the pouches and extend across each of the pouches.

20. The textile of claim 19, wherein the textile is a longitudinal tubular graft.

21. The textile of claim 20, wherein a cross-sectional view of the longitudinal tubular graft through the pouch has 4 layers of woven material.

22. The textile of claim 20, wherein the at least one pouch is circumferentially disposed about the longitudinal tubular graft.

23. The textile of claim 20 wherein the longitudinal tubular graft portion is continuous with an inner tubular wall of the pouch forming a continuous tube, and wherein the continuous tube extends from the first end of the graft to the second end of the longitudinal tubular graft.

24. The textile of claim 19, wherein the textile does not contain a seam between the pouch and the longitudinal textile portion.

25. The textile of claim 19, wherein an element is disposed within the pouch.

26. The textile of claim 25, wherein the element is a metal wire.

27. The textile of claim 19, wherein the yarns are resorbable or non-absorbable, and wherein the yarns are selected from the group consisting of a natural material, a synthetic material, a metal, and any combination thereof.

28. The textile of claim 19, wherein the at least one textile portion and the at least one pouch are woven from the same set of warp ends.

29. The textile of claim 19, wherein the at least one textile portion is woven from a first set of warp ends and the at least one pouch is woven from a portion of the first set of warp ends and at least one additional set of warp ends.

30. The textile of claim 19, wherein the at least one textile portion is woven from a first set of weft yarns and the at least one pouch is woven from at least a portion of the first set of weft yarns and at least one additional set of weft yarns.

31. The textile of claim 30, wherein a material of the first set of weft yarns is different from a material of the at least one additional set of weft yarns.

32. The textile of claim 19, wherein the at least one textile portion is woven from a first set of weft yarns, the first pouch is woven from at least a portion of the first set of weft yarns and a second set of weft yarns, and the second pouch is woven from at least a portion of the first set of weft yarns and either the second set of weft yarns or a third set of weft yarns.

* * * * *